(12) United States Patent
Akmandor et al.

(10) Patent No.: US 10,986,994 B2
(45) Date of Patent: Apr. 27, 2021

(54) STRESS DETECTION AND ALLEVIATION SYSTEM AND METHOD

(71) Applicant: The Trustees of Princeton University, Princeton, NJ (US)

(72) Inventors: Ayten Ozge Akmandor, Plainsboro, NJ (US); Niraj K. Jha, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 321 days.

(21) Appl. No.: 15/857,981

(22) Filed: Dec. 29, 2017

(65) Prior Publication Data

US 2018/0184901 A1    Jul. 5, 2018

Related U.S. Application Data

(60) Provisional application No. 62/442,517, filed on Jan. 5, 2017.

(51) Int. Cl.
*A61B 5/00* (2006.01)
*A61B 5/16* (2006.01)
(Continued)

(52) U.S. Cl.
CPC .......... *A61B 5/0006* (2013.01); *A61B 5/0024* (2013.01); *A61B 5/0205* (2013.01); *A61B 5/165* (2013.01); *A61B 5/4836* (2013.01); *A61B 5/4848* (2013.01); *G16H 20/70* (2018.01); *G16H 40/63* (2018.01); *G16H 40/67* (2018.01); *G16H 50/20* (2018.01); *G16H 50/70* (2018.01); *A61B 5/02405* (2013.01); *A61B 5/02438* (2013.01); *A61B 5/4884* (2013.01); *G16H 10/60* (2018.01); *G16H 50/30* (2018.01)

(58) Field of Classification Search
CPC ....................................................... A61B 5/165
USPC ........................................................ 434/236
See application file for complete search history.

(56) References Cited

U.S. PATENT DOCUMENTS 9,792,823 B2 * 10/2017 Zhuang ................... G10L 15/26
10,198,505 B2 * 2/2019 Frank .................... G06Q 10/101
(Continued)

OTHER PUBLICATIONS

Brownlee, J. (Mar. 19, 2014). Feature Selection to Improve Accuracy and Decrease Training Time. Retrieved Nov. 21, 2020, from https://machinelearningmastery.com/feature-selection-to-improve-accuracy-and-decrease-training-time/ (Year: 2014).*

(Continued)

*Primary Examiner* — Jerry-Daryl Fletcher
*Assistant Examiner* — Daniel E Lane
(74) *Attorney, Agent, or Firm* — Meagher Emanuel Laks Goldberg & Liao, LLP.

(57) ABSTRACT

According to various embodiments, a stress detection and alleviation (SoDA) system for a user is disclosed. The system includes a SoDA device configured with one or more processors that receive wearable medical sensor (WMS) data from a plurality of WMSs. The processors are programmed to remove one or more artifacts from the WMS data, extract a set of features from the WMS data, remove correlated features from the extracted features to obtain a reduced set of features, classify the reduced set of features in order to determine whether the user is stressed, and generate a response based on whether the user is stressed.

24 Claims, 16 Drawing Sheets

(51) Int. Cl.
| | |
|---|---|
| G16H 20/70 | (2018.01) |
| A61B 5/0205 | (2006.01) |
| A61B 5/024 | (2006.01) |
| G16H 10/60 | (2018.01) |
| G16H 40/63 | (2018.01) |
| G16H 50/70 | (2018.01) |
| G16H 50/20 | (2018.01) |
| G16H 40/67 | (2018.01) |
| G16H 50/30 | (2018.01) |

(56) References Cited

U.S. PATENT DOCUMENTS

| | | | |
|---|---|---|---|
| 2005/0069936 A1* | 3/2005 | Diamond | A61K 31/00 435/6.16 |
| 2005/0176057 A1* | 8/2005 | Bremer | G16B 20/00 435/6.16 |
| 2010/0209892 A1* | 8/2010 | Lin | G09B 19/167 434/71 |
| 2010/0211270 A1* | 8/2010 | Chin | B62D 6/007 701/44 |
| 2014/0266939 A1* | 9/2014 | Baringer | H01Q 21/28 343/729 |
| 2014/0273858 A1* | 9/2014 | Panther | A61B 5/0002 455/41.2 |
| 2014/0275850 A1* | 9/2014 | Venkatraman | A61B 5/4812 600/301 |
| 2014/0275852 A1* | 9/2014 | Hong | A61B 5/02427 600/301 |
| 2014/0275854 A1* | 9/2014 | Venkatraman | A61B 5/721 600/301 |
| 2014/0278220 A1* | 9/2014 | Yuen | G01B 21/16 702/150 |
| 2014/0278229 A1* | 9/2014 | Hong | A63B 71/06 702/160 |
| 2014/0288435 A1* | 9/2014 | Richards | A61B 5/02427 600/479 |
| 2014/0316305 A1* | 10/2014 | Venkatraman | A61B 5/1112 600/595 |
| 2014/0358012 A1* | 12/2014 | Richards | A61B 5/4812 600/479 |
| 2015/0005911 A1* | 1/2015 | Lake, II | G06Q 50/22 700/91 |
| 2015/0093729 A1* | 4/2015 | Plans | G06F 16/683 434/236 |
| 2015/0173631 A1* | 6/2015 | Richards | A61B 5/7282 600/479 |
| 2015/0199010 A1* | 7/2015 | Coleman | A61B 5/0006 345/156 |
| 2016/0055236 A1* | 2/2016 | Frank | G06Q 30/02 707/748 |
| 2016/0196758 A1* | 7/2016 | Causevic | G09B 5/00 434/236 |
| 2016/0242690 A1* | 8/2016 | Principe | A61B 5/04012 |
| 2017/0188864 A1* | 7/2017 | Drury | A61B 5/0408 |
| 2017/0249434 A1* | 8/2017 | Brunner | G06F 19/3418 |
| 2017/0365101 A1* | 12/2017 | Samec | G02B 27/017 |

OTHER PUBLICATIONS

J. Wijsman, B. Grundlehner, H. Liu, H. Hermens and J. Penders, "Towards mental stress detection using wearable physiological sensors," 2011 Annual International Conference of the IEEE Engineering in Medicine and Biology Society, Boston, MA, 2011, pp. 1798-1801, doi: 10.1109/IEMBS.2011.6090512. (Year: 2011).*
Kumar, V. (2014). Feature Selection: A literature Review. The Smart Computing Review, 4(3). doi:10.6029/smartcr.2014.03.007 (Year: 2014).*
Ayten Ozge Akmandor et al. "Keep the Stress Away with SoDA: Stress Detection and Alleviation System", IEEE Transactions on Multi-Scale Computing Systems, vol. 3, No. 4, pp. 269-282; Oct.-Dec. 2017.
J. Wijsman, B. Grundlehner, H. Liu, J. Penders, and H. Hermens, "Wearable physiological sensors reflect mental stress state in office-like situations," in Proc. IEEE Conf. Affective Computing and Intelligent Interaction, pp. 600-605, 2013.
J. A. Healey and R. W. Picard, "Detecting stress during real-world driving tasks using physiological sensors," IEEE Trans. Intelligent Transportation Syst., vol. 6, No. 2, pp. 156-166, 2005.
J. Zhang, H. Tang, D. Chen, and Q. Zhang, "Destress: Mobile and remote stress monitoring, alleviation, and management platform," in Proc. IEEE Global Commun. Conf., pp. 2036-2041, 2012.
K. Plarre, A. Raij, S. M. Hossain, A. A. Ali, M. Nakajima, M. Al'absi, E. Ertin, T. Kamarck, S. Kumar, M. Scott, D. Siewiorek, A. Smailagic, and L. E. Wittmers, "Continuous inference of psychological stress from sensory measurements collected in the natural environment," in Proc. IEEE Int. Conf. Inform. Process. in Sensor Networks, pp. 97-108, 2011.
S. Begum, M. U. Ahmed, P. Funk, N. Xiong, B. Scheele, M. Lindén, and M. Folke, "Diagnosis and biofeedback system for stress," in Proc. IEEE Int. Wkshp. Wearable Micro and Nano Technologies for Personalized Health, pp. 17-20, 2009.
J. Choi and R. Gutierrez-Osuna, "Using heart rate monitors to detect mental stress," in Proc. IEEE Int. Wkshp. Wearable and Implantable Body Sensor Networks, pp. 219-223, 2009.
A. Fernandes, R. Helawar, R. Lokesh, T. Tari, and A. V. Shahapurkar, "Determination of stress using blood pressure and Galvanic skin response," in Proc. IEEE Int. Conf. Commun. and Network Technologies, pp. 165-168, 2014.
A. Ghosh, M. Danieli, and G. Riccardi, "Annotation and prediction of stress and workload from physiological and inertial signals," in Proc. Int. Conf. IEEE Eng. in Medicine and Biology Soc., pp. 1621-1624, 2015.
V. Sandulescu and R. Dobrescu, "Wearable system for stress monitoring of firefighters in special missions," in Proc. IEEE E-Health and Bioengineering Conf., pp. 1-4, 2015.
A. Muaremi, B. Amrich, and G. Tröster, "Towards measuring stress with smartphones and wearable devices during workday and sleep," J. BioNanoScience, vol. 3, No. 2, pp. 172-183, 2013.
J. Choi, B. Ahmed, and R. Gutierrez-Osuna, "Development and evaluation of an ambulatory stress monitor based on wearable sensors," IEEE Trans. Inform. Technology in Biomedicine, vol. 16, No. 2, pp. 279-286, 2012.
P. Melillo, M. Bracale, and L. Pecchia, "Nonlinear heart rate variability features for real-life stress detection. Case study: Students under stress due to university examination," J. Biomedical Eng. Online, vol. 10, No. 1, p. 1, 2011.
G. Tanev, D. B. Saadi, K. Hoppe, and H. B. Sorensen, "Classification of acute stress using linear and non-linear heart rate variability analysis derived from sternal ECG," in Proc. Int. Conf. IEEE Eng. Medicine and Biology Soc., pp. 3386-3389, 2014.
J. Zhai and A. Barreto, "Stress detection in computer users based on digital signal processing of noninvasive physiological variables," in Proc. IEEE Int. Conf. Eng. Medicine and Biology Soc., pp. 1355-1358, 2006.
Q. Xu, T. L. Nwe, and C. Guan, "Cluster-based analysis for personalized stress evaluation using physiological signals," IEEE J. Biomedical and Health Informatics, vol. 19, No. 1, pp. 275-281, 2015.
A. Sano and R. W. Picard, "Stress recognition using wearable sensors and mobile phones," in Proc. IEEE Conf. Affective Computing and Intelligent Interaction, pp. 671-676, 2013.
J. Choi and R. Gutierrez-Osuna, "Estimating mental stress using a wearable cardio-respiratory sensor," IEEE Sensors J., pp. 150-154, 2010.

* cited by examiner

| Sensor | Abbreviation | Unit | Number of Features |
|---|---|---|---|
| Electrocardiogram | ECG | mV | 57 |
| Galvanic Skin Response | GSR | mS | 16 |
| Respiration | RESP | 1/min | 9 |
| Blood Oximeter | BO | % | 2 |
| Blood Pressure | BP | mmHg | 6 |

|   | Feature | Sensor | Threshold |
|---|---|---|---|
| 1 | ECG-derived respiration rate | ECG | 8.9 |
| 2 | Mean of skin conductance amplitude | GSR | 8.9 |
| 3 | Standard deviation of skin conductance amplitude | GSR | 8.9 |
| 4 | Sum of amplitudes of skin conductance respenses above the threshold (continuous decomposition analysis) | GSR | 8 |
| 5 | Mean of tonic activity | GSR | 8 |
| 6 | Maximum positive deflection | GSR | 8 |
| 7 | Mean of respiration duration | RESP | 8 |
| 8 | RMS of respiration signal | RESP | 8.9 |
| 9 | Median of respiration duration | RESP | 8 |
| 10 | Mean of blood oxygen level | BO | 8.9 |
| 11 | Mean of systolic blood pressure | BP | 8.9 |
| 12 | Variance of systolic blood pressure | BP | 8.9 |
| 13 | Mean of diastolic blood pressure | BP | 8.9 |
| 14 | Mean of MAP | BP | 8.9 |
| 15 | Varaince of MAP | BP | 8.9 |

*FIG. 13*

|   | Generalized Model | | Individualized Model | | | |
|---|---|---|---|---|---|---|
|   | (≥ 8) | (≥ 9) | (≥ 8) | | (≥ 9) | |
|   |   |   | Mean | Median | Mean | Median |
| kNN1 | 11.0 | 9.0 | 8.4 | 9.0 | 6.5 | 6.0 |
| kNN2 | 11.0 | 9.0 | 8.5 | 9.0 | 6.7 | 6.0 |
| kNN3 | 11.0 | 9.0 | 8.5 | 9.0 | 6.6 | 6.0 |
| kNN4 | 11.0 | 9.0 | 8.0 | 9.0 | 6.5 | 6.0 |
| SVM | 11.0 | 9.0 | 6.7 | 7.0 | 6.7 | 7.0 |

*FIG. 14*

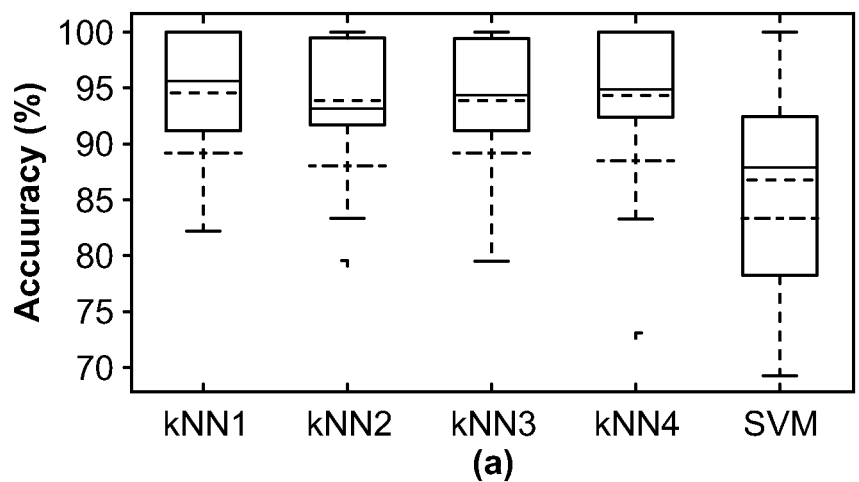
(a)
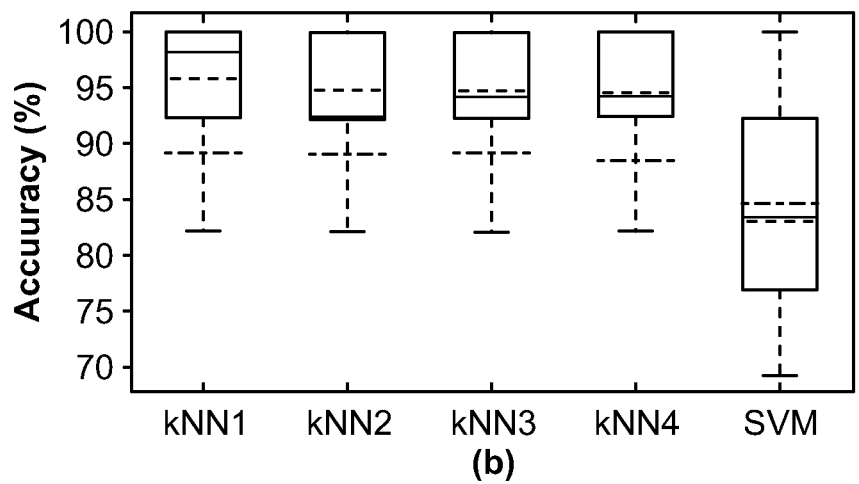
(b)
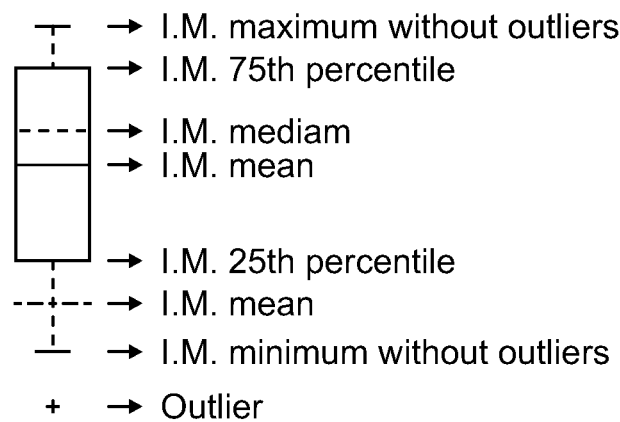
— → I.M. maximum without outliers
— → I.M. 75th percentile
- - → I.M. mediam
— → I.M. mean
— → I.M. 25th percentile
- - → I.M. mean
— → I.M. minimum without outliers
+ → Outlier
I.M. → Individual Model
G.M. → General Model
(c)
*FIG. 16*

| Sensor | #Features (≥ 8) | #Features (≥ 9) | Timp Elapsed (ms) Feature Extractioin (≥ 8) | Timp Elapsed (ms) Feature Extractioin (≥ 9) |
|---|---|---|---|---|
| ECG | 1 | 1 | 1.5 | 1.5 |
| GSR | 5 | 2 | 11.4 | 9.9 |
| RESP | 3 | 1 | 46.1 | 38.3 |
| BO | 1 | 1 | 35.3 | 35.3 |
| BP | 5 | 5 | 205.2 | 205.2 |
| Total | 15 | 10 | 299.5 | 290.2 |

*FIG. 17*

Stress Alleviation Protocol

Given: *therapySet*, set of the stress alleviation techniques.
1: *therapy ← null, k ← 0, flag ← 0*
2: for *i = 1, ..., length(therapySet)*
3:    *therapy ← therapySet(i)*
4:    *Delay (30sec.)*
5:    *Compute selected N feature values*
6:    *Compute k, number of features showing stress relief*
7:    if $k \geq N/2$
8:       *Delay (30sec.)*
9:       *Compute selected N feature values*
10:       *Compute k*
11:       if $k \geq N/2$
12:          *flag ← 1*
13:          return
14:       end
15:    end
16: end
17: if *flag = 0, when none of the stress alleviation techniques is effective*
18: *Give warning to the user*
19: return
20: end

*FIG. 18*

|       | Mean |      | Median |      | 25th |      | 75th |      |
|-------|------|------|--------|------|------|------|------|------|
|       | T2   | T5   | T2     | T5   | T2   | T5   | T2   | T5   |
| R-R   | 0.52 | 0.51 | 0.51   | 0.48 | 0.43 | 0.41 | 0.59 | 0.60 |
| HR    | 0.18 | 0.19 | 0.18   | 0.18 | 0.13 | 0.13 | 0.22 | 0.24 |
| LF/HF | 0.06 | 0.06 | 0.03   | 0.03 | 0.01 | 0.01 | 0.06 | 0.08 |
|       | T3   | T7   | T3     | T7   | T3   | T7   | T3   | T7   |
| R-R   | 0.54 | 0.52 | 0.53   | 0.51 | 0.42 | 0.44 | 0.64 | 0.62 |
| HR    | 0.17 | 0.18 | 0.16   | 0.17 | 0.11 | 0.12 | 0.22 | 0.21 |
| LF/HF | 0.06 | 0.10 | 0.02   | 0.03 | 0.01 | 0.01 | 0.06 | 0.06 |
|       | T4   | T8   | T4     | T8   | T4   | T8   | T4   | T8   |
| R-R   | 0.51 | 0.52 | 0.49   | 0.49 | 0.41 | 0.42 | 0.61 | 0.58 |
| HR    | 0.19 | 0.18 | 0.18   | 0.18 | 0.13 | 0.14 | 0.23 | 0.23 |
| LF/HF | 0.05 | 0.07 | 0.03   | 0.03 | 0.01 | 0.01 | 0.05 | 0.07 |

*FIG. 19*

|       | Mean |      | Median |      | 25th |      | 75th |      |
|-------|------|------|--------|------|------|------|------|------|
|       | T2   | T5   | T2     | T5   | T2   | T5   | T2   | T5   |
| R-R   | 0.51 | 0.55 | 0.47   | 0.53 | 0.40 | 0.42 | 0.57 | 0.62 |
| HR    | 0.21 | 0.19 | 0.21   | 0.18 | 0.15 | 0.13 | 0.26 | 0.24 |
| LF/HF | 0.05 | 0.05 | 0.02   | 0.02 | 0.01 | 0.01 | 0.05 | 0.04 |
|       | T3   | T7   | T3     | T7   | T3   | T7   | T3   | T7   |
| R-R   | 0.54 | 0.55 | 0.53   | 0.55 | 0.43 | 0.46 | 0.62 | 0.64 |
| HR    | 0.18 | 0.19 | 0.18   | 0.17 | 0.13 | 0.12 | 0.24 | 0.22 |
| LF/HF | 0.09 | 0.07 | 0.03   | 0.02 | 0.01 | 0.01 | 0.10 | 0.05 |
|       | T4   | T8   | T4     | T8   | T4   | T8   | T4   | T8   |
| R-R   | 0.52 | 0.55 | 0.50   | 0.51 | 0.40 | 0.43 | 0.63 | 0.68 |
| HR    | 0.21 | 0.19 | 0.20   | 0.19 | 0.13 | 0.11 | 0.26 | 0.25 |
| LF/HF | 0.05 | 0.05 | 0.03   | 0.03 | 0.02 | 0.01 | 0.07 | 0.07 |

*FIG. 20*

|     | Mean | | Median | | 25th | | 75th | |
| --- | --- | --- | --- | --- | --- | --- | --- | --- |
|     | T2 | T5 | T2 | T5 | T2 | T5 | T2 | T5 |
| R-R | 0.93 | 0.93 | 0.93 | 0.93 | 0.86 | 0.92 | 1.00 | 0.94 |
| HR  | 0.04 | 0.04 | 0.04 | 0.04 | 0.00 | 0.04 | 0.08 | 0.05 |
| LF/HF | 0.00 | 0.28 | 0.00 | 0.28 | 0.00 | 0.03 | 0.01 | 0.54 |
| Inh | 0.34 | 0.24 | 0.34 | 0.24 | 0.29 | 0.14 | 0.40 | 0.34 |
|     | T3 | T7 | T3 | T7 | T3 | T7 | T3 | T7 |
| R-R | 0.98 | 1.03 | 0.98 | 1.03 | 0.97 | 1.00 | 0.99 | 1.06 |
| HR  | 0.02 | -0.02 | 0.02 | -0.02 | 0.01 | -0.03 | 0.02 | 0.00 |
| LF/HF | 0.84 | 0.13 | 0.84 | 0.13 | 0.69 | 0.08 | 1.00 | 0.19 |
| Inh | 0.70 | 0.55 | 0.70 | 0.55 | 0.39 | 0.44 | 1.00 | 0.65 |
|     | T4 | T8 | T4 | T8 | T4 | T8 | T4 | T8 |
| R-R | 0.82 | 1.02 | 0.82 | 1.02 | 0.81 | 0.96 | 0.83 | 1.07 |
| HR  | 0.11 | -0.01 | 0.11 | -0.01 | 0.10 | -0.04 | 0.12 | 0.02 |
| LF/HF | 0.05 | 0.16 | 0.05 | 0.16 | 0.04 | 0.09 | 0.06 | 0.24 |
| Inh | 0.04 | 0.74 | 0.04 | 0.74 | 0.00 | 0.60 | 0.08 | 0.87 |

FIG. 21

|     | Mean | | Median | | 25th | | 75th | |
| --- | --- | --- | --- | --- | --- | --- | --- | --- |
|     | T2 | T5 | T2 | T5 | T2 | T5 | T2 | T5 |
| R-R | 0.93 | 0.98 | 0.93 | 0.98 | 0.85 | 0.93 | 1.00 | 1.04 |
| HR  | 0.04 | 0.01 | 0.04 | 0.01 | 0.00 | -0.02 | 0.09 | 0.04 |
| LF/HF | 0.12 | 0.31 | 0.12 | 0.31 | 0.04 | 0.11 | 0.20 | 0.51 |
| Inh | 0.55 | 0.28 | 0.55 | 0.28 | 0.09 | 0.01 | 1.00 | 0.55 |
|     | T3 | T7 | T3 | T7 | T3 | T7 | T3 | T7 |
| R-R | 0.97 | 1.21 | 0.97 | 1.21 | 0.96 | 1.14 | 0.98 | 1.29 |
| HR  | 0.02 | -0.11 | 0.02 | -0.11 | 0.01 | -0.15 | 0.03 | -0.08 |
| LF/HF | 0.19 | 0.06 | 0.19 | 0.06 | 0.00 | -0.01 | 0.38 | 0.13 |
| Inh | 0.52 | 1.19 | 0.52 | 1.19 | 0.11 | 0.79 | 0.92 | 1.59 |
|     | T4 | T8 | T4 | T8 | T4 | T8 | T4 | T8 |
| R-R | 0.93 | 1.01 | 0.93 | 1.01 | 0.91 | 0.96 | 0.95 | 1.06 |
| HR  | 0.04 | 0.00 | 0.04 | 0.00 | 0.03 | -0.03 | 0.05 | 0.03 |
| LF/HF | 0.10 | 0.14 | 0.10 | 0.14 | 0.09 | 0.09 | 0.10 | 0.20 |
| Inh | 0.27 | 0.71 | 0.27 | 0.71 | 0.00 | 0.26 | 0.53 | 1.17 |

FIG. 22

|   | Generalized Model | Individualized Model |
|---|---|---|
| 1 | Micro-meditation | Warm Stone |
| 2 | Good News | Good News |
| 3 | Warm Stone | Micro-meditation |

*FIG. 23*

STRESS DETECTION AND ALLEVIATION SYSTEM AND METHOD

CROSS-REFERENCE TO RELATED APPLICATIONS

This application claims priority to provisional application 62/442,517, filed on Jan. 5, 2017, which is herein incorporated by reference in its entirety.

BACKGROUND OF THE INVENTION

The present invention relates generally to stress detection and alleviation systems and, more particularly, to a stress relief system that continuously monitors stress levels via data from wearable medical sensors and utilizes machine learning systems based on supervised feature selection, unsupervised dimensionality reduction, and classification to detect and mitigate stress as it arises without the need for user intervention.

Stress is a serious health problem that afflicts a large fraction of humanity. In the United States, three out of four visits to the doctor are due to stress-related disorders. In Europe, stress is reported to be the second most common health problem. Stress also has a severe adverse impact on the United States' economy. According to the American Institute of Stress (AIS), each year $300 billion is spent on the treatment of stress-induced disorders.

Stress can be divided into two parts: stressor and reaction. Stressor is the activity or effect that triggers a change in the physiological parameter values of the human body. Reaction is the deviation of these parameter values from their normal levels. When confronted with a stressor, the body raises an alarm that results in a stress response. The stress response of the body depends on the duration for which the stressor is active. With long and frequent stress responses, a person becomes more likely to develop one or more serious health problems. For example, excessive exposure to stress may result in depression, cardiovascular diseases, sleep disorders, degradation in the immune system, or cancer, as nonlimiting examples. In addition to stressor duration, personal traits also play a significant role in stress response. These traits have an impact on physiological signals, and indirectly on the emotional condition.

As such, it is desirable to have immediate stress alleviation when a stress response is detected. Stress alleviation should ideally be tailored to the individual to have maximum impact.

SUMMARY OF THE INVENTION

According to various embodiments, a stress detection and alleviation (SoDA) system for a user is disclosed. The system includes a SoDA device configured with one or more processors that receive wearable medical sensor (WMS) data from a plurality of WMSs. The processors are programmed to remove one or more artifacts from the WMS data, extract a set of features from the WMS data, remove correlated features from the extracted features to obtain a reduced set of features, classify the reduced set of features in order to determine whether the user is stressed, and generate a response based on whether the user is stressed.

According to various embodiments, a method for stress detection and alleviation (SoDA) for a user of a SoDA device is disclosed. The SoDA device includes one or more processors. The method includes receiving wearable medical sensor (WMS) data from a plurality of WMSs, removing one or more artifacts from the WMS data, extracting a set of features from the WMS data, removing correlated features from the extracted features to obtain a reduced set of features, classifying the reduced set of features in order to determine whether the user is stressed, and generating a response based on whether the user is stressed.

According to various embodiments, a non-transitory computer-readable medium having stored thereon a computer program for execution by a processor configured to perform a method for stress detection and alleviation of a user is disclosed. The method includes receiving wearable medical sensor (WMS) data from a plurality of WMSs, removing one or more artifacts from the WMS data, extracting a set of features from the WMS data, removing correlated features from the extracted features to obtain a reduced set of features, classifying the reduced set of features in order to determine whether the user is stressed, and generating a response based on whether the user is stressed.

Various other features and advantages will be made apparent from the following detailed description and the drawings.

BRIEF DESCRIPTION OF THE DRAWINGS

In order for the advantages of the invention to be readily understood, a more particular description of the invention briefly described above will be rendered by reference to specific embodiments that are illustrated in the appended drawings. Understanding that these drawings depict only exemplary embodiments of the invention and are not, therefore, to be considered to be limiting its scope, the invention will be described and explained with additional specificity and detail through the use of the accompanying drawings, in which:

FIG. 13 is a table showing selected feature sets for input to the principal component analysis (PCA) stage according to an embodiment of the present invention;

FIG. 14 is a table showing PCA reduced dimensions for the generalized embodiment and statistics of reduced dimensions for the individualized embodiment according to embodiments of the present invention;

FIG. 16 is a chart showing classification accuracy according to an embodiment of the present invention;

FIG. 17 is a table showing time elapsed during feature extraction according to an embodiment of the present invention;

FIG. 18 is a protocol for stress alleviation according to an embodiment of the present invention;

FIG. 19 is a table showing statistics of physiological signals in a generalized embodiment for 0-50 seconds according to an embodiment of the present invention;

FIG. 20 is a table showing statistics of physiological signals in a generalized embodiment for 60-120 seconds according to an embodiment of the present invention;

FIG. 21 is a table showing statistics of physiological signals in an individualized embodiment for 0-50 seconds according to an embodiment of the present invention;

FIG. 22 is a table showing statistics of physiological signals in an individualized embodiment for 60-120 seconds according to an embodiment of the present invention; and FIG. 23 is a table showing the order of stress reduction techniques according to an embodiment of the present invention.

DETAILED DESCRIPTION OF THE INVENTION

Figure 1:
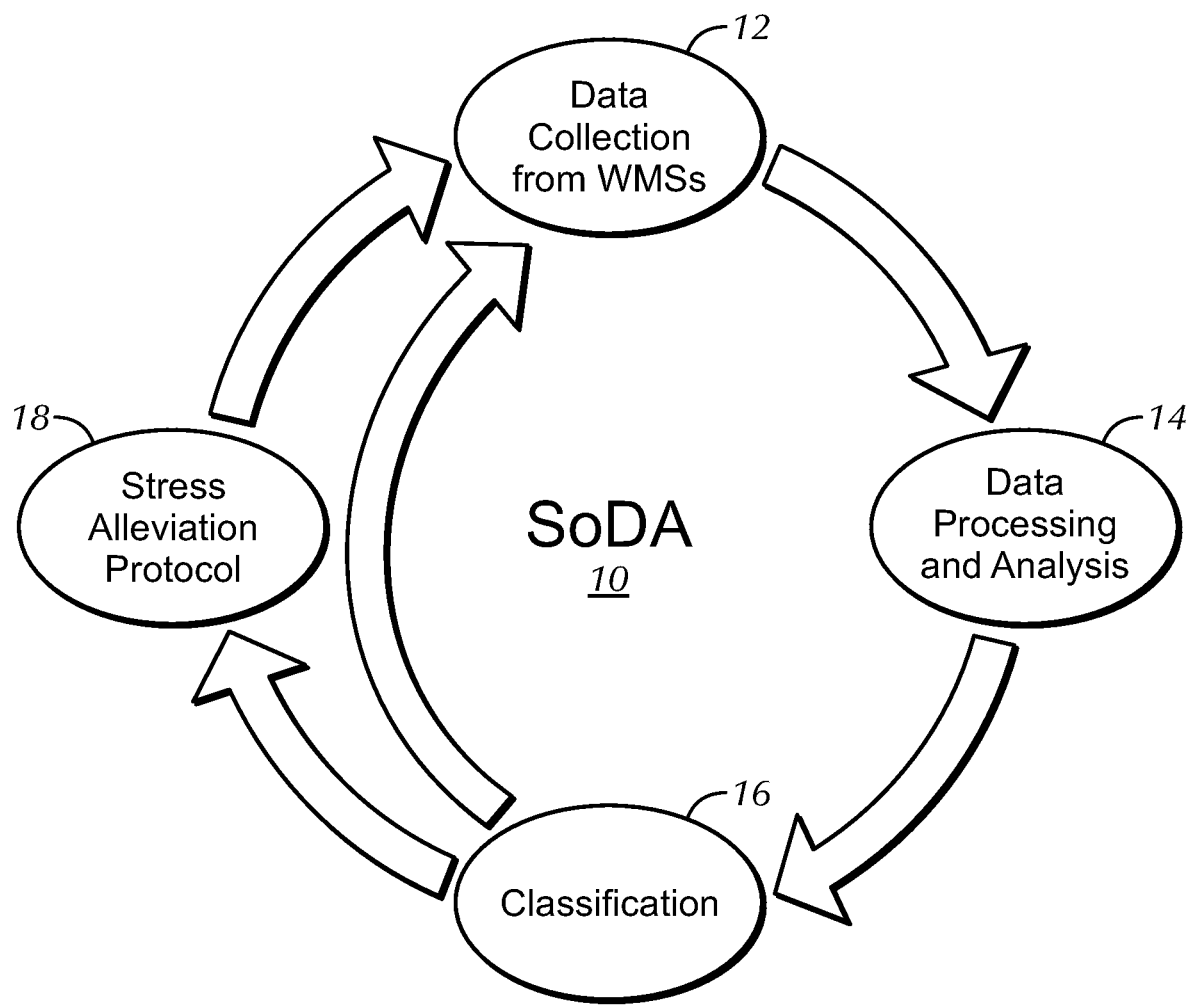
FIG. 1 is a flowchart of the stress detection and alleviation system according to an embodiment of the present invention.

According to various embodiments, disclosed herein is a stress detection and alleviation system (referred to herein as "SoDA"). As shown broadly in FIG. 1, SoDA 10 detects stress and then employs a stress alleviation technique based on the stress characteristics of the person. First, data is collected from wearable medical sensors in block 12, then the data is processed and analyzed in block 14, and then classified in block 16 in order to provide a particular stress alleviation protocol in block 18. The process can continuously repeat itself as stress levels are monitored, as illustrated by the arrows shown in FIG. 1.

Stress characteristics are deduced from physiological signals obtained through wearable medical sensors (WMSs). WMSs may be utilized for ECG, GSR, respiration rate, blood pressure, and blood oximeter, as nonlimiting examples. However, more sophisticated and other types of WMSs can be easily incorporated into SoDA as and when they become available. Use of WMSs offers several advantages. First, WMSs continuously collect data from the human body, making it possible to detect a stress response quickly. Second, they also enable real-time stress mitigation. Alternatively, since the WMS data are typically communicated to an on-body device, such as a smartphone, and thereon to a health server that is accessible to a doctor, it has the potential to enhance the ability of a doctor to intervene significantly faster than currently possible. Third, if stress-induced disorders can be significantly reduced, it may bend the national health expenditure curve downwards.

The stress detection and mitigation system disclosed herein can offer two options to the user: "generalized" and "individualized". In the generalized embodiment, the system detects and alleviates stress by using a predetermined stress model based on data obtained from a population of individuals. The individualized embodiment is configured based on the particular user's stress response. The generalized embodiment becomes active just after turning on the system, whereas the individualized embodiment requires training data from the user for modeling purposes. However, the individualized embodiment is more accurate in discerning if the user is stressed since it is trained on WMS data obtained from the user.

System Overview

Figure 2:
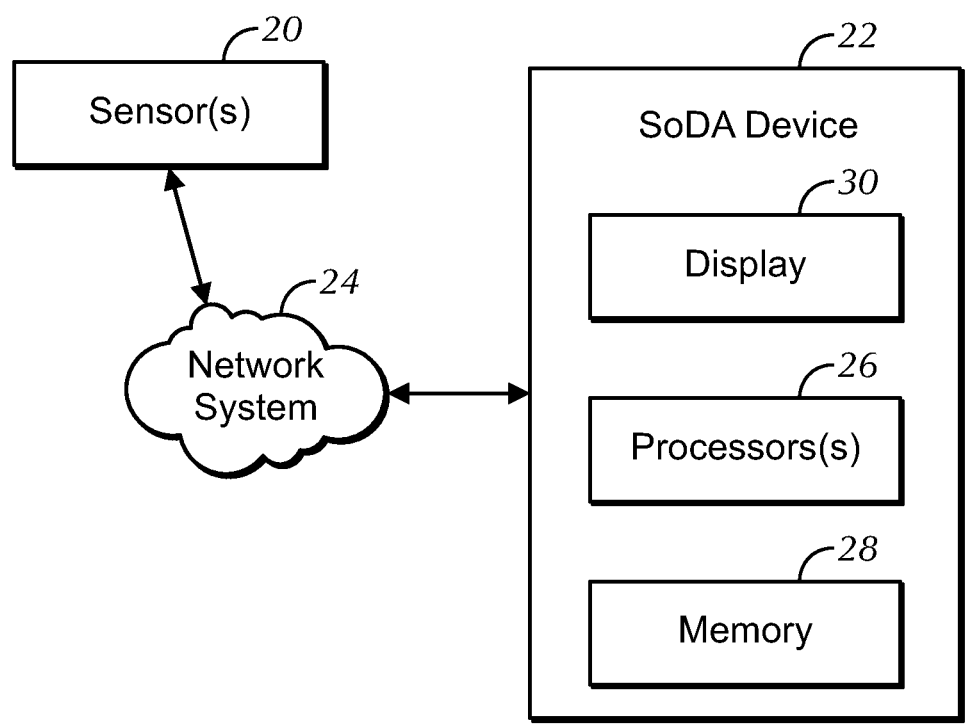
FIG. 2 is a block diagram of the stress detection and alleviation system according to an embodiment of the present invention.

A simplified block diagram of a SoDA system 10 is shown in FIG. 2 according to an embodiment of the present invention. Each element will be discussed in greater detail in the forthcoming sections. SoDA 10 includes one or more wearable medical sensors (WMSs) shown generally by reference number 20. The WMSs may be utilized for ECG, GSR, respiration rate, blood pressure, and blood oximeter, as nonlimiting examples.

The sensors 20 may be connected to a SoDA device 22 via a network system 24. The sensors 20 may also be integrated into the SoDA device 22 in alternative embodiments. If the sensors 20 are integrated into the SoDA device 22, then a network system 24 is not required. The SoDA device 22 may be implemented in a variety of configurations including general computing devices such as desktop computers, laptop computers, tablets, network appliances, or mobile devices such as mobile phones, smart phones, or smart watches. The SoDA device 22 includes one or more processors 26 for performing specific functions and memory 28 for storing those functions. Particularly, the processors 26 process data received from the sensors 20 to generate stress mitigation data, to be discussed in greater detail in the forthcoming sections. This data may be output via a display 30 on the SoDA device 22.

The network system 24 may be implemented as a single network or a combination of multiple networks. Network system 24 may include but is not limited to wireless telecommunications networks, WiFi, Bluetooth, Zigbee, or other communications networks. Network system 24 may be a wired network as well.

Figure 3:
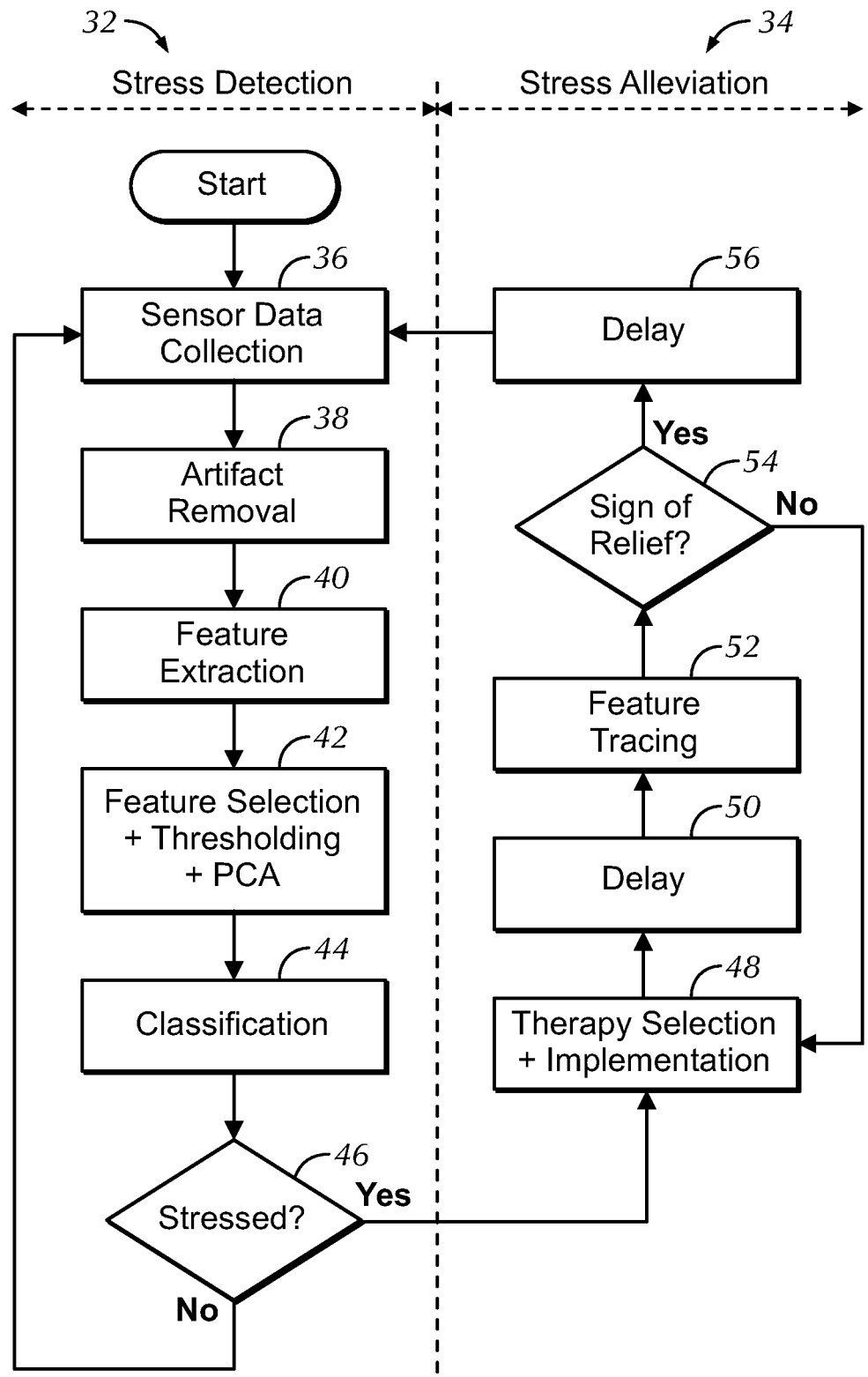
FIG. 3 is a flowchart of the stress detection and alleviation system according to an embodiment of the present invention.

A simplified flow chart of the SoDA system 10 is shown in FIG. 3, where each step will be discussed in greater detail in the forthcoming sections. SoDA 10 includes a stress detection section 32 and a stress alleviation section 34. SoDA 10 starts at step 36 with sensor data collection from the one or more sensors 20. After collecting physiological signals from the sensors 20, the SoDA device 22 removes artifacts from the data, i.e., de-noises the data, at step 38. Then, various features are extracted from the data at step 40. Since some of these features may be correlated, not all of them are used for stress classification, since correlations lead to redundancy and may impact stress classification performance negatively. Therefore, at step 42, a reduced set of features is obtained via feature selection, thresholding, and principal component analysis. At step 44, the reduced set of features is classified via machine-learning systems, such as support vector machine or k-nearest neighbor, as nonlimiting examples. Based on the classified features, at step 46, SoDA 10 queries whether the user is stressed. If no, SoDA 10 returns to the sensor data collection step 36. If yes, SoDA moves to the stress alleviation section 34.

The stress alleviation section 34 starts with step 48, where a particular stress relief therapy is selected and implemented. Stress relief therapy includes but is not limited to micro-meditation, reading good news, listening to classical music, deep breathing, and repeating words/suggestions in the mind. A brief delay is then implemented at step 50, because stress relief is not instantaneous. After the delay, at step 52, relevant feature values are traced to determine if the user is still stressed. This leads to a query at step 54 whether the user shows signs of stress relief. If, no SoDA 10 returns to step 48 to select and implement a different stress relief therapy. If yes, after a brief delay at 56, SoDA 10 returns to the stress detection section 32 by continuing to collect sensor data at step 36.

Motivation

Stress is unavoidable and can be triggered by various events. For example, stressors may lurk at work, in expectations, or simply in various ordinary circumstances, e.g., traffic jams, time pressure, lack of sleep, pollution, inconsiderate people, and excess noise. When exposed to long periods of stress or excessive stress, an individual's health is impacted negatively, becoming more susceptible to lifelong health problems, such as diabetes, hypertension, heart disease, etc. Thus, it is important to detect and alleviate stress as quickly as possible.

As such, the aim of the system disclosed herein is to continuously track the human stress level and try to maintain it within normal levels. Continuous stress measurement is made possible through inference on WMS data. Based on user preference (generalized or individualized), upon detection of stress, an appropriate sequence of stress reduction techniques is selected and suggested to the user. If the feature values extracted from the WMS data collected after the application of the first stress alleviation technique show a tendency towards a relaxed state, the system stays with the technique; otherwise, it suggests the next technique and reevaluates.

In the system disclosed herein, SoDA, stress characteristics of the user are modeled with the help of four different stressors. With a distinctive feature selection performed based on WMS data, when the individual is subjected to these stressors, high accuracy in stress detection is obtained. All four stressors are evaluated with and without the stress alleviation techniques. Their impact is evaluated after the participant's stress level attains approximately the same level as just before the application of stress alleviation. While performing the task, the stressor is not removed in the alleviation stage. This enables more realistic and reliable comparisons among the stress alleviation techniques. Moreover, since different individuals may respond in different degrees to various stress alleviation techniques, the system responds to a user's needs adaptively and quickly by selecting the best sequence of such techniques.

Stress and Health

Stress is a wide-ranging and complex topic that does not have a specific definition. According to one definition, stress may be the relationship between the person and a situation, which adversely impacts the happiness and health of the sufferer. Another definition of stress is that it is a physiological reaction that aims to protect the individual from possible threats emanating from the environment. These definitions indicate that stress arises from a threatening situation. An individual's body activates its defense mechanism to adapt to or overcome the stressful circumstance. When the stressor disappears, our body returns to normal operation. However, this recovery takes some time since stress results in chemical changes in the individual's body. Thus, continuous exposure to stress prevents the body from returning to normal, and thus has long-term health consequences, ranging from cardiovascular to psychological problems.

WMSs and Physiological Parameters

WMSs are noninvasive and autonomous devices that are used to monitor human health. They are called wearable since they are placed on the human body or clothing. They come in various forms: patches, bandages, glasses, rings, bracelets, as nonlimiting examples. WMSs can monitor posture, fetal health, heart disease, obesity, diabetes, epilepsy, sleep quality, cigarette smoking, etc.

The physiological parameters related to stress include but are not limited to heart rate, blood pressure, skin conductivity, respiration rate, blood oxygen level, electromyograph (EMG) of trapezius muscles, pupil diameter, and cortisol level. Obtaining heart rate, blood pressure, skin conductivity, respiration rate, and blood oxygen level requires minimal obtrusion. As such, they are the parameters for the preferred embodiment of the disclosed system. However, other parameters may still be utilized in other embodiments.

Figure 4:
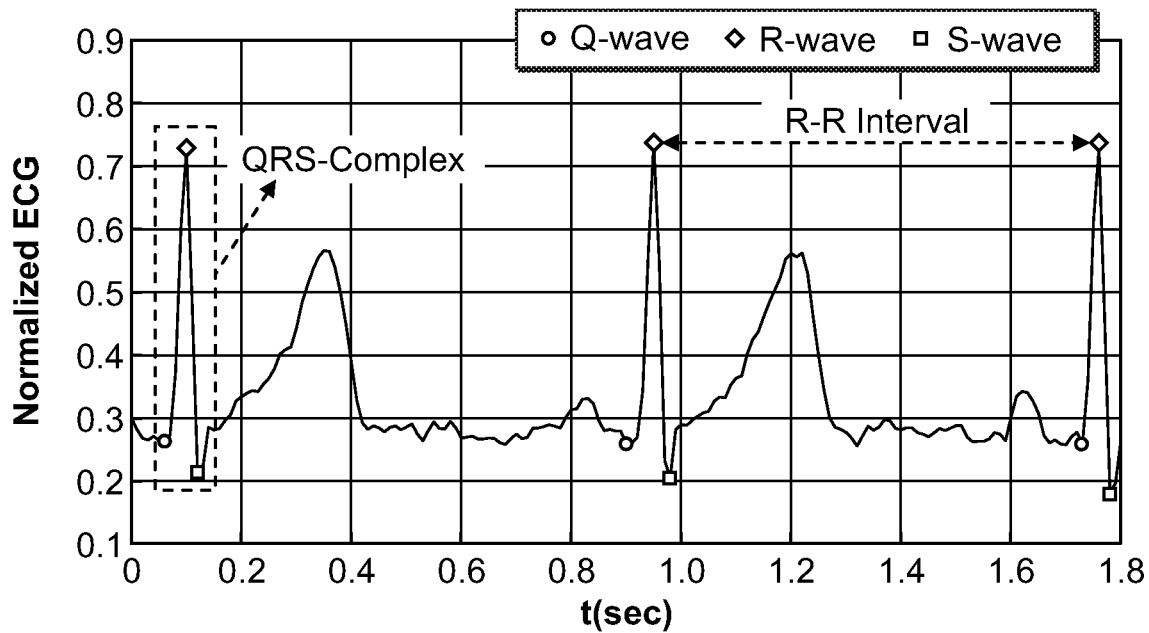
FIG. 4 is an example of an ECG signal according to an embodiment of the present invention.

Electrocardiogram (ECG):

An ECG sensor measures the electrical activity of the heart during a cardiac cycle. It is noninvasively obtained by relying on body fluids as conductors and comparing the potential difference between the electrodes. An example of an ECG signal is shown in FIG. 4. A cardiac cycle is composed of P-Q-R-S-T waves. The most detectable part of the ECG signal is the Q-R-S complex. In this complex, the first negative deflection is called the Q-wave, which is followed by a large positive deflection called the R-wave, and the next negative deflection called the S-wave. Generally, the Q-R-S complex lasts for 60-100 milliseconds in adults. From the ECG signal, values for various parameters, such as the heart rate (HR), heart rate variability (HRV), R-R interval, etc., can be derived. Deviations in the values of these parameters in consecutive cycles may indicate stress.

Figure 5:
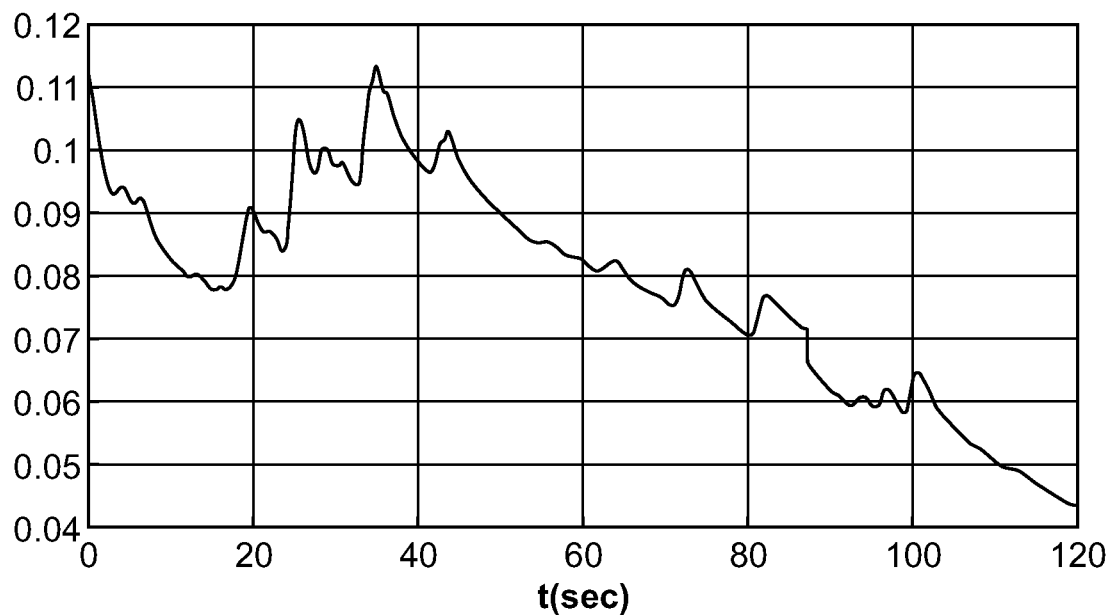
FIG. 5 is an example of a normalized GSR signal according to an embodiment of the present invention.

Galvanic Skin Response (GSR):

GSR indicates the change in electrical characteristics of the skin due to perspiration from the body. It measures skin conductance (SC) noninvasively by applying a low constant voltage through the electrodes. An example of a normalized GSR signal is shown in FIG. 5. The measured SC is composed of two electrodermal activities: phasic and tonic. Phasic activity is the high frequency component and thus varies quickly, whereas tonic activity is the low frequency component and thus changes more slowly. Stressful situations can cause sweat production, which changes skin conductance.

Figure 6:
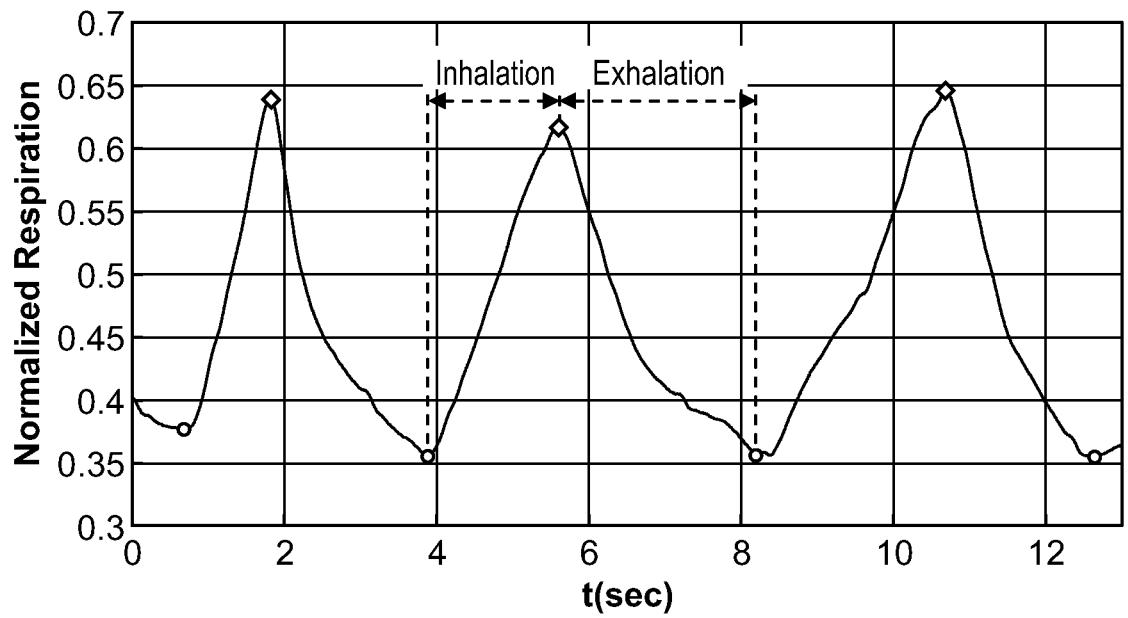
FIG. 6 is an example waveform of a respiration signal according to an embodiment of the present invention.

Respiration Monitor (RESP):

Respiration is composed of inhalation and exhalation. An example waveform of the respiration signal is shown in FIG. 6. During respiration, oxygen is transmitted to the cells and the accumulated carbon dioxide is removed. The normal respiration rate for adults is 12-16 breaths per minute. Although respiration rate can be obtained through different methods, the respiration monitor utilized herein measures thoracic expansion to obtain respiratory information. Stressors influence the duration and amplitude of inhalation and exhalation.

Blood Oximeter (BO):

A blood oximeter noninvasively measures the blood oxygen level with the help of light-emitting diodes (LEDs). Blood consists of hemoglobin molecules. When these molecules have different oxygen levels, they lead to different levels of absorption of the light emitted through the LEDs. The blood oximeter uses this property to emit light from one side of a fingertip or earlobe and analyzes the received signal emanating from the other side to assess the blood oxygen level. Stress also has an impact on this level.

Blood Pressure Monitor (BP):

Blood pressure is the force exerted on blood vessels of the circulatory system. It has two components: systolic and diastolic. Systolic blood pressure indicates the pressure when the heart pumps blood into the arteries, whereas diastolic blood pressure indicates the pressure when the arteries withstand the blood flow. Both systolic and diastolic blood pressures can be obtained through the blood pressure monitor. The normal range for the systolic blood pressure is 90-120 mmHg, and the normal range for the diastolic blood pressure is 60-80 mmHg. In the presence of a stressor, systolic and diastolic blood pressures deviate from their baseline levels.

Figure 7:
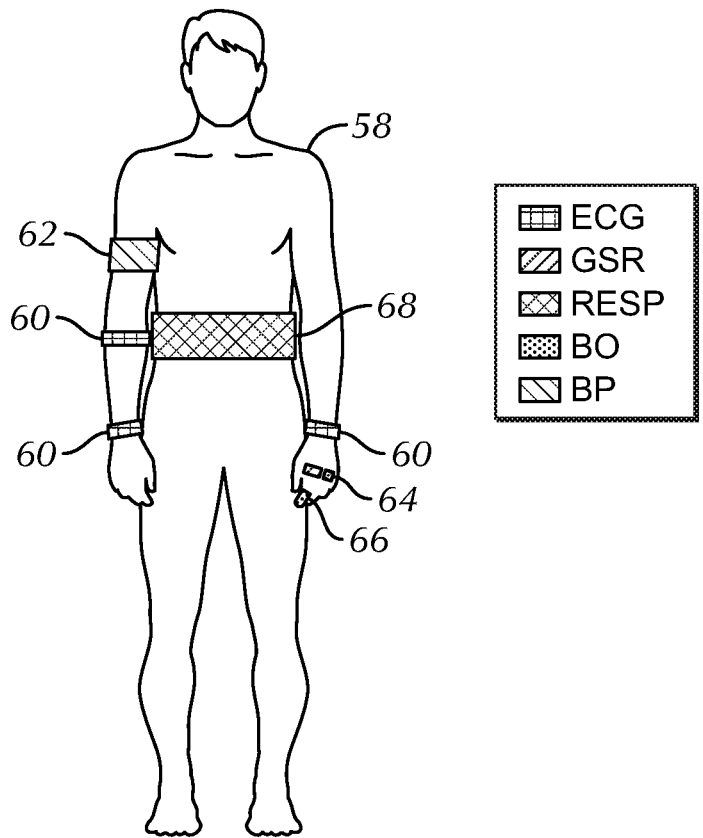
FIG. 7 is a diagram showing an example of on-body positions of WMSs according to an embodiment of the present invention.

Physiological signals may be collected through the five WMSs discussed above: ECG, blood pressure monitor, GSR, respiration monitor, and blood oximeter, in a preferred embodiment of the present invention. However, alternative embodiment may utilize other WMSs. ECG, GSR, and respiration monitor has a sampling rate of 100 Hz, whereas blood oximeter has a sampling rate of 1 Hz. However, other sampling rates may be used in alternative embodiments. Blood pressure is not measured continuously. When the individual performs a stress-inducing task, blood pressure measurements are taken in the beginning, middle, and end. However, for the baseline and individual-under-rest parts of the experiments, to be discussed in further detail below, blood pressure is measured in the beginning and at the end. The body placement of the chosen WMSs takes into account both the comfort of the individual and the accuracy of the measurements. An example of on-body positions of WMSs on an individual 58 are shown in FIG. 7. The ECG 60 and blood pressure monitor 62 are placed on the arms of the individual 58. The GSR 64 and blood oximeter 66 are placed on the finders of the individual 58. The respiratory monitor 68 is placed around the waist of the individual 58.

It should be noted that alternative embodiments may have different WMSs, different WMS positions, or have all WMSs integrated into a single WMS sensor platform. Furthermore, alternative embodiments may utilize different physiological signal data as inputs.

Experimental Procedure for Feature Extraction

Figure 8:
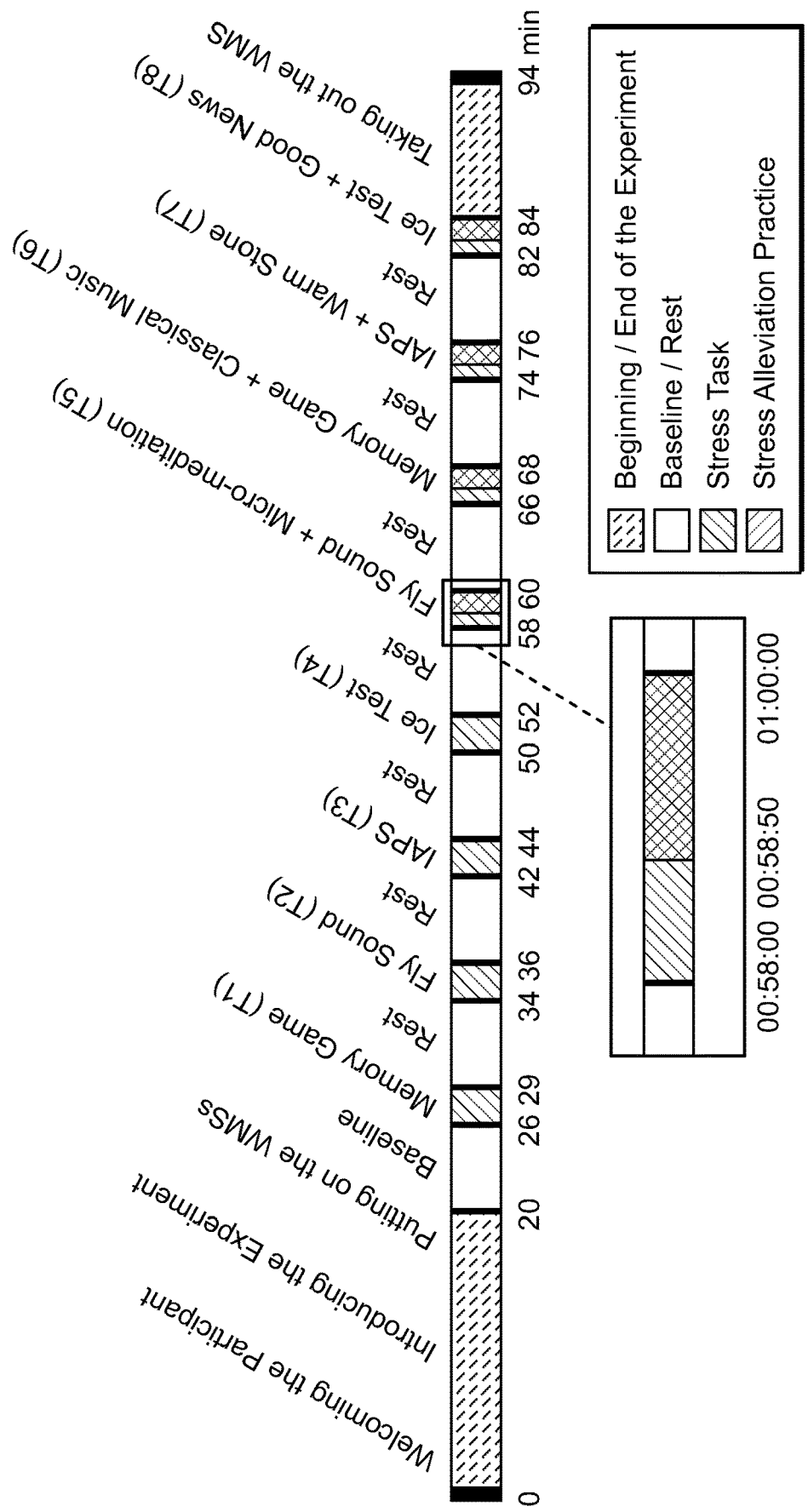
FIG. 8 is a diagram showing an example experimental procedure according to an embodiment of the present invention.

For each participant, the laboratory session took approximately 90 minutes. FIG. 8 summarizes the experimental procedure. The session starts by welcoming and asking the participant to sit on a comfortable chair. Then, the experimental procedure and on-body positions of WMSs are explained to the participant in detail. Once wearing the sensors, the participant is reminded of the importance of silence and correct body posture. The participant is encouraged to ask questions. Upon ensuring that the participant is comfortable with the experimental setup and procedure, the experiment commences.

Baseline:

This is the first stage of the experiment. It is performed to obtain the original levels of the physiological signals. In this stage, the participant is asked to look at the black screen and relax.

Rest:

A rest period is introduced in between two tests to calm the participant down. A stressful task pushes the physiological signals to deviate from their original levels, thus requiring a rest period to recover. As in the baseline stage, the participant is asked to look at the black screen and relax.

Memory Game:

This game is played on a computer. The participant is shown 40 cards that are flipped back. Two cards are selected in every round. If the cards match, they remain in the face-up position. If they do not match, then both cards are flipped back and another round commences. The participant is given two minutes to complete this task.

Fly Sound:

In this stage, the participant is asked to listen to the sound of a fly buzzing around, with a black screen shown to prevent distraction.

International Affective Picture System (IAPS):

In this task, the participant is shown pictures from the IAPS Database. The pictures are selected based on the affective ratings specified in the IAPS Technical Manual. Before displaying the pictures, an informative slide ("Get Ready for the Next Slide") is shown for five seconds. Then, the picture is displayed for seven seconds. This procedure is repeated for a total of 10 pictures. Two sets of tests are performed without (T3) and with (T7) stress mitigation techniques. The corresponding picture numbers for the two sets are as follows:

Set 1: 1304, 3060, 3170, 3266, 6260, 6313, 9040, 9300, 9413, 9635.

Set 2: 1525, 3053, 3080, 6520, 9220, 9405, 9410, 9570, 9921, 9940.

Ice Test:

In this test, the participant is asked to place the right hand on top of an ice-filled container. In the event of discomfort, the participant is encouraged to raise the hand and place it back on the ice or finish the test. The test is not started until the ice has melted partially.

Stress Mitigation Techniques

SoDA offers various stress mitigation techniques: classical music, micro-meditation, warm stone, and good news, as nonlimiting examples. Alternative embodiments may incorporate other stress mitigation techniques as well. In the individualized embodiment, an individual-specific order of these techniques is employed, whereas in the generalized embodiment, a fixed sequence is used for each individual. In order to obtain the most effective sequence, the four stress-inducing tasks are carried out with and without stress alleviation techniques.

As shown in FIG. 8, in tasks T1-T8, stressors are applied for 0-120 seconds; however, in tasks T5-T8, in addition to the stressors, the alleviation techniques are also employed in the 50-120 second range.

Classical Music:

During the memory game (T6), classical music is played starting at the 50th second. The composition set includes but is not limited to Benjamin Godard's "Berceuse" and Frederic Chopin's "II. Romance".

Micro-Meditation:

Micro-meditation is a short-duration practice for nurturing self-awareness. It can be employed in various forms. In the experiment, in the presence of the fly sound stressor (T5), the participant is asked to close the eyes and relax various body parts starting from the feet to face. As before, this technique is employed starting at the 50th second of the task and instructions related to body parts that need to be relaxed are provided during the meditation.

Warm Stone:

In this stress mitigation technique, using IAPS pictures as stressors (T7), the participant is asked to hold in the palm a warm stone of size approximately 9×8×2 cm. The stone may be other sizes in other embodiments. The stone is warmed up by placing it in boiling water for two minutes. Then, it is taken out, dried, and placed on its side for another two minutes. At the 50th second of the task, the participant is given the warm stone, with continuing display of selected IAPS pictures on the screen.

Good News:

While the participant is performing the ice test, positive and optimistic news are displayed on the screen. Task T8 is started with a black screen. Starting at the 50th second, good news accompanied by a corresponding picture is shown for 10 seconds. A total of seven news items are displayed.

Preprocessing and Feature Extraction

Figure 9:
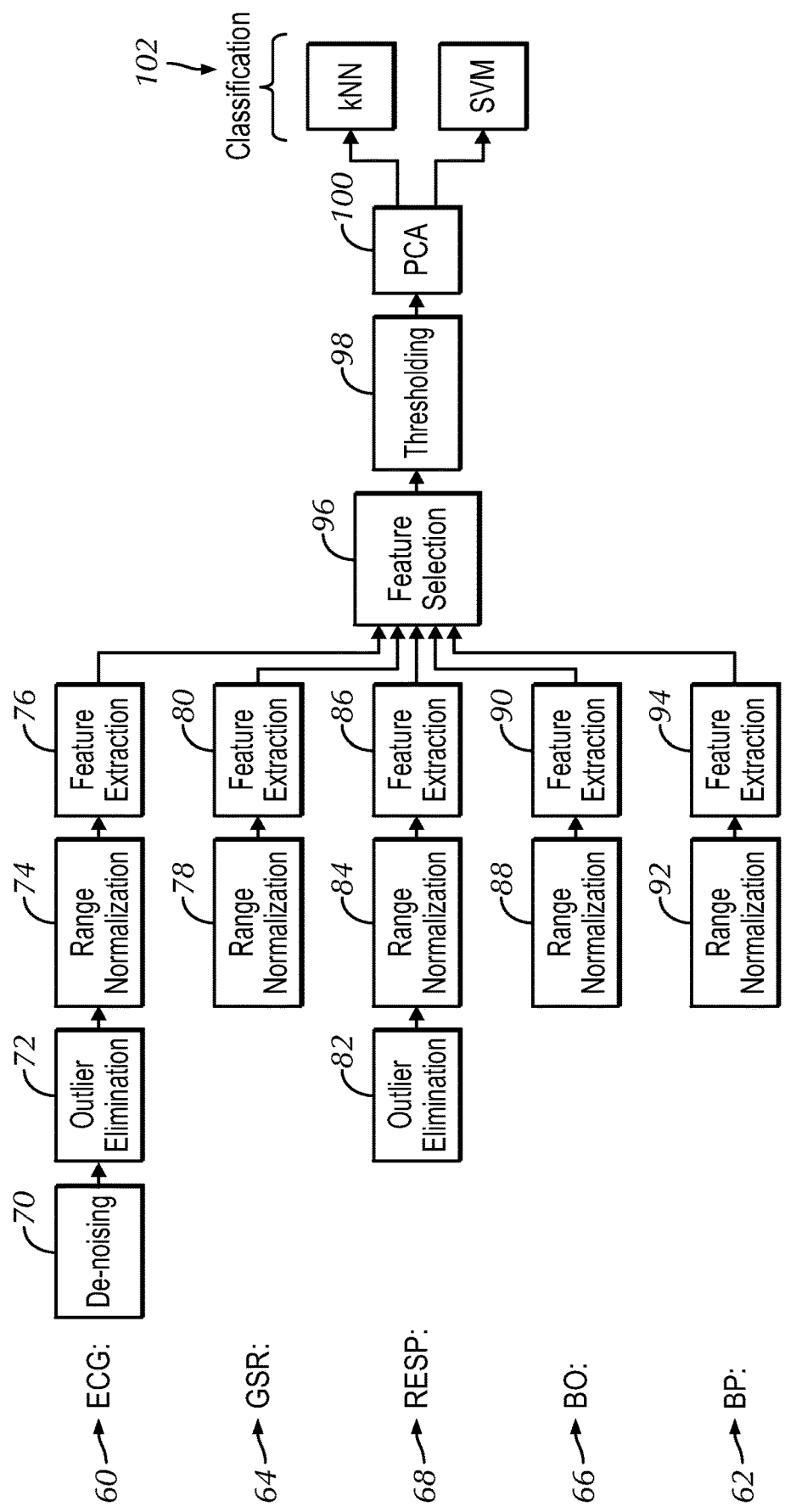
FIG. 9 is a flowchart showing data processing according to an embodiment of the present invention.

To obtain the performance measures, the data obtained from the participants is analyzed. The dataset for each participant is composed of 24×2 minutes of measurements collected through the five WMSs. FIG. 9 shows how the data from these WMSs are processed, as described below.

ECG 60:

Processing from the ECG 60 includes the following steps: de-noising 70, outlier elimination 72, range normalization 74, and feature extraction 76.

The ECG signal needs to be de-noised first at step 70. The de-noising steps target baseline wander, power-line interference, muscle noise, etc. Baseline wander is a very low frequency component that can be caused by perspiration, respiration, and body movements. Given that the lowest observed heart rate is approximately 40 bpm (0.67 Hz), a cut-off frequency of 0.5 Hz is selected. A zero-phase high-pass filter is employed based on this cut-off frequency. In order to remove muscle noise and the aliased components of power-line interference, the FFT of the ECG signal is plotted. When a peak is observed in the absolute FFT, a notch filter is used to remove the noise. The frequency corresponding to the highest amplitude in the peak is selected as the center frequency of the notch filter.

Following the de-noising step 70, the outliers are replaced with the upper/lower thresholds that are derived from the data in step 72. Moreover, at step 74, range normalization shown in the following equation is carried out to eliminate the variability in the physiological signal levels of the participants.

$$d'_i = \frac{d_i - \min(d)}{\max(d) - \min(d)}$$

After signal preprocessing is complete, at step 76, a total of 57 ECG features are extracted. This is done by detecting the Q-R-S complex and calculating the corresponding features (e.g., mean, variance, quartile deviation, 80th percentile, etc.) using code implemented in a computing program such as MatLab. For heart rate variability related features, a heart rate variability analysis program such as Kubios HRV is utilized. Intervals for frequency domain computations are determined as very low frequency (VLF, 0-0.04 Hz), low frequency (LF, 0.04-0.15 Hz), and high frequency (HF, 0.15-0.4 Hz). Following the computations in MatLab and Kubios, the extracted feature values are combined and stored with the ones obtained through other WMSs.

GSR 64:

Processing from the GSR 64 includes the following steps: range normalization 78, and feature extraction 80.

The data obtained from the GSR sensor 64 are first subjected to range normalization via the same equation above at step 78. Then, mean, median, and standard deviation of the data are calculated using MatLab. Moreover, continuous and discrete decomposition analyses are carried out using a skin conductance data analysis program such as Ledalab. A total of 16 features are extracted from GSR data at step 80.

Respiration Monitor 68:

Processing from the respiration monitor 68 includes the following steps: outlier elimination 82, range normalization 84, and feature extraction 86.

The outliers of the data obtained from the respiration monitor are replaced with upper or lower thresholds at step 82. After removing the data artifacts, range normalization is performed with the same equation above at step 84. Then, feature values are calculated using MatLab. From the respiration data, a total of nine features are extracted at step 86: mean, median, and quartile deviation of the respiration duration, root mean square (RMS) of the respiration signal, mean of inhalation and exhalation durations, mean and median of the ratio of inhalation-to-exhalation duration, and mean of stretch.

Blood Oximeter 66:

Processing from the blood oximeter 66 includes the following steps: range normalization 88 and feature extraction 90.

The data obtained from the blood oximeter are also first range-normalized by the above equation at step 88. Then, two features are extracted at step 90: mean and variance.

Blood Pressure Monitor 62:

Processing from the blood pressure monitor 62 includes the following steps: range normalization 92 and feature extraction 94.

This monitor 62 measures the systolic/diastolic pressures and derives the mean arterial pressure (MAP). In order to get comparable feature values across the participants, range normalization as shown above is used in step 92. Then, the corresponding mean and variance are calculated. A total of six features are obtained from the blood pressure measurements at step 94.

Figures 10, 11:
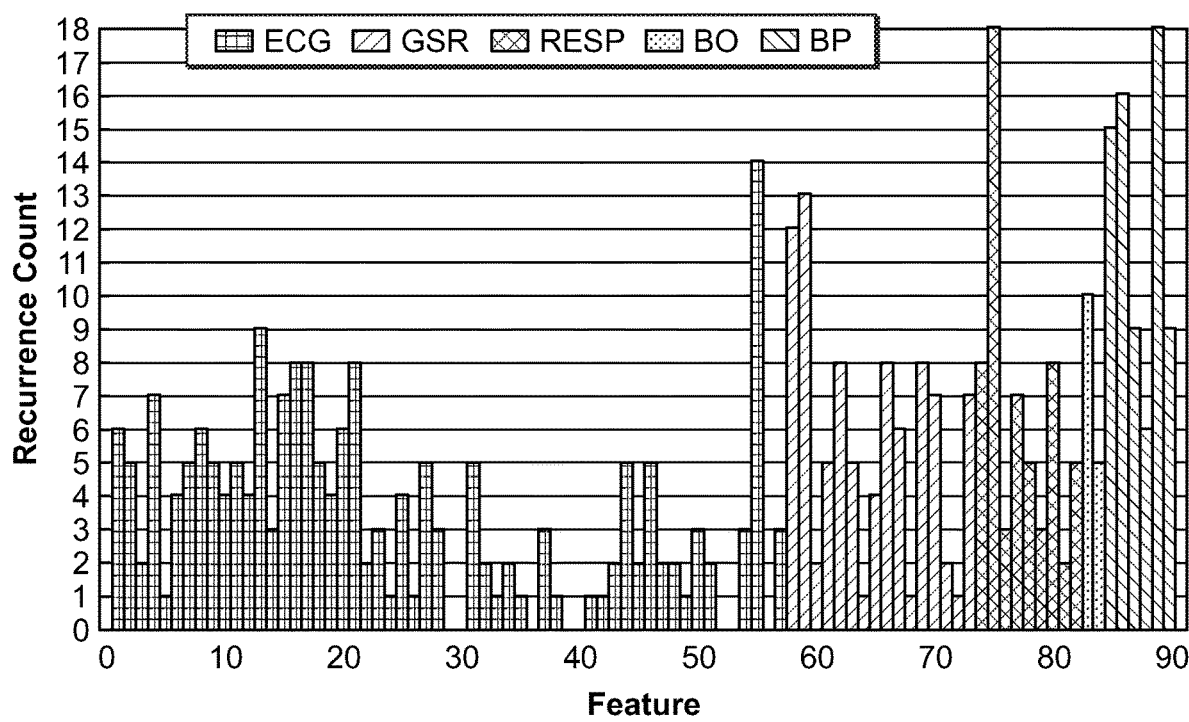
FIG. 10 is a table summarizing various details of the WMSs including features extracted according to an embodiment of the present invention.
FIG. 11 is a graph showing the recurrence count of features according to an embodiment of the present invention.

Various details of the WMSs are summarized in FIG. 10, including their abbreviations, units, and the total number of features extracted.

Feature Selection, Thresholding, PCA, and Classification

After preprocessing, a total of 90 features from the physiological signals collected by the five WMSs are extracted. Since some of these features may be correlated and correlations lead to redundancy, which impacts classification performance negatively, not all of them are used for stress detection. Hence, the data is divided into three parts: first part for training, second part for validation of chosen parameters, and third part for testing. Supervised attribute selection is applied to the training part using a machine learning software such as Weka 3.8.0 at step 96. This includes the steps of forward feature selection and subset evaluation. In forward feature selection, the system starts with an empty set and searches for features in the forward direction in a greedy fashion. In subset evaluation, each feature is analyzed in terms of its individual contribution to accuracy and its redundancy with respect to the other features. The output of attribute selection 96 is a set of features that minimizes redundancy while improving accuracy. This procedure 96 is carried out for each of the participants.

The reduced set of features obtained thus far is then subjected to principal component analysis (PCA) at step 100. PCA 100 transforms the input information into a group of new orthogonal variables that are linearly uncorrelated. These variables are called principal components. The first principal component has the largest variance, hence includes the largest amount of information about the input data. The second principal component is orthogonal to the first one and has the second largest possible variance. Under the condition of orthogonality, the remaining components are then calculated. Since the majority of data can be represented by the first n components, the remaining ones can be ignored. This enables compression of the data. Thus, PCA 100 is used to extract the most relevant information from the data, and shown to have a positive effect on classification accuracy.

For the present embodiment, the most important information has already been extracted through supervised attribute selection. However, due to the finite size of training data available, the optimal feature set obtained based on the training dataset may not be optimal for the testing dataset. In order to address this problem, a thresholding step 98 is included prior to the PCA step 100. The reduced sets of features from all participants' data are combined and the number of times each feature appears calculated. Only features that appear more than a predefined threshold are selected and provided as input to PCA 100 for dimensionality reduction. This helps to eliminate features that do not carry too much information.

However, the combined set may include redundant features and the training data may not be enough to determine the optimal feature set. Since PCA 100 is an unsupervised method, it does not take into account the labels of the training data. By calculating orthogonal components and choosing the first n that represent a majority of the data, the negative impact on supervised feature selection of the finite-sized training data is abated. In other words, supervised feature selection 96 is used as a coarse sieve, then PCA 100 is employed as a fine sieve. The number of principal components, n, is determined based on each participant's data separately. The principal components are added one by one to the training data. At the (n+1)-th component, if the classification accuracy on the validation data does not increase, then n is taken to be the optimal number of principal components.

The data obtained after the PCA step 100 are fed to the classification stage 102 for each of the participants. Due to their widespread applicability and excellent performance, support vector machine (SVM) and k-nearest neighbor (kNN) are employed for binary classification. However, other classification methods may be implemented in alternative embodiments. In SVM, classification is done by finding a hyperplane that separates the n-dimensional data into two classes and maximizes the margin. However, since the data is not linearly separable here, a radial basis function (RBF) kernel is utilized. The RBF kernel maps the data to a higher-dimensional space where they are linearly separable.

In kNN, the k-nearest neighbors are determined based on a distance metric (e.g., Euclidean, Minkowski, etc.) and classification is performed using majority voting. In the present embodiment, Euclidean distance is used as the distance measure. Moreover, since the generalized embodiment is obtained by combining each individual's data, the optimal k is different for the individualized and generalized embodiments. Thus, to have comparable results, kNN is performed for a k value spanning 1 to 4. It should be noted alternative embodiments are not limited to kNN with k=1, 2, 3, or 4. Analysis based on different k values demonstrates the consistent performance of SoDA.

As such, 90 features were obtained from the physiological data collected by the WMSs and the best subset for each of the participants is obtained. The number of features in this subset ranged from 8 to 22. These reduced sets are combined and the number of times each feature appears is counted. The recurrence count of the features is shown in FIG. 11. This figure indicates that all five physiological signals are indicators of stress. However, compared with the others, the recurrence count of the ECG features is smaller. This is because the total number of features extracted from ECG outnumbers the number of features extracted from the other four physiological signals. In other words, since ECG features provide more options to choose from, the result is a more spread distribution. To get around this problem, different recurrence count thresholds are used for ECG and GSR+RESP+BO+BP derived features. Only the features that are above these thresholds are found to be useful for a larger set of participants and selected for the modeling of stress.

Figure 12:
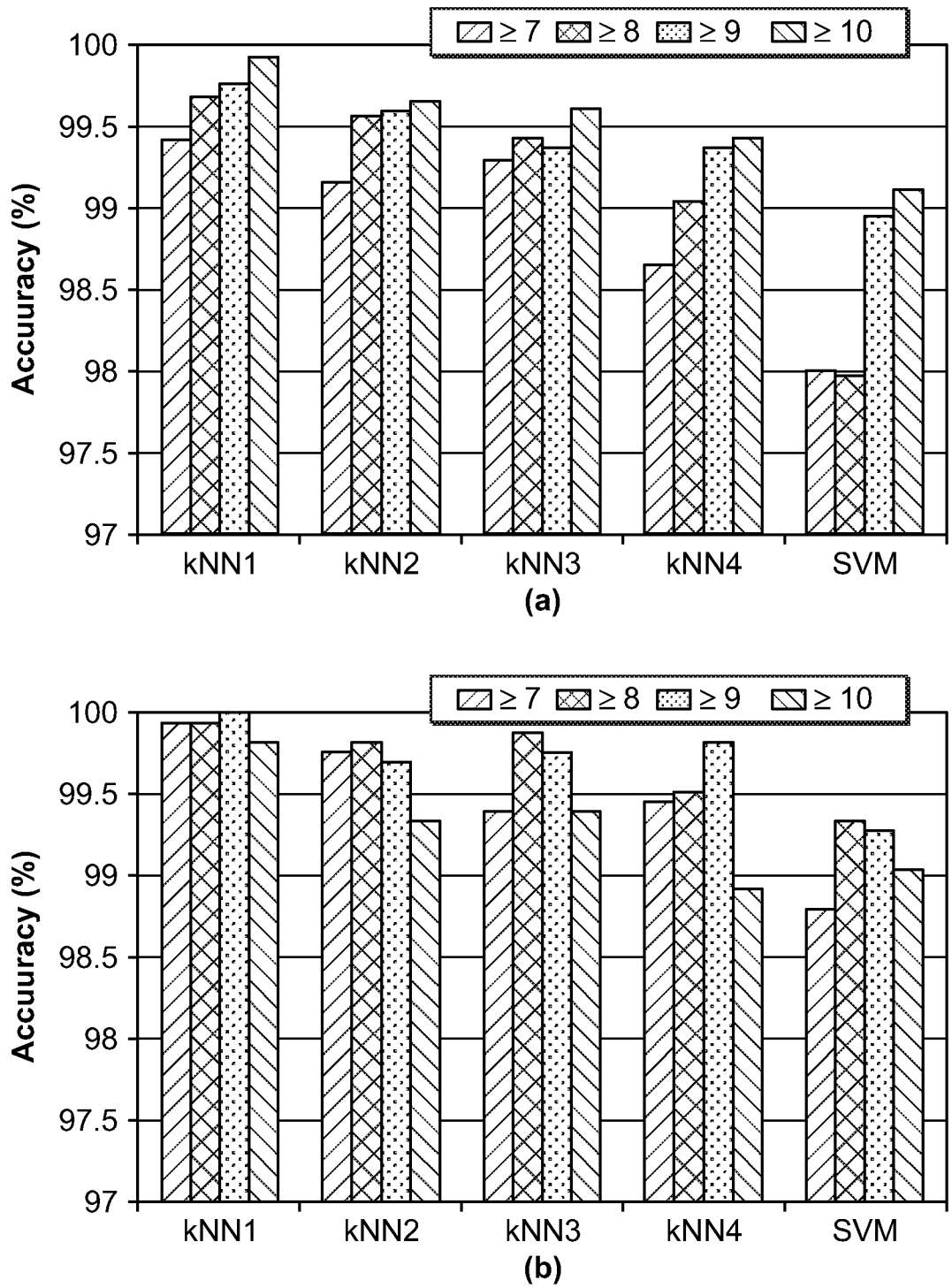
FIG. 12 is a graph showing accuracy with respect to recurrence count limits according to an embodiment of the present invention.

In FIG. 12, the accuracy of the stress detection stage is analyzed for various thresholds of ECG (in FIG. 12(*a*)) and GSR+RESP+BO+BP (in FIG. 12(*b*)), respectively. Since a threshold of ten for ECG and eight/nine for GSR+RESP+BO+BP lead to the best or near-best accuracy in all the cases, they are chosen as the thresholds. Thus, features with ECG recurrence count of ten or above and GSR+RESP+BO+BP recurrence count of eight/nine or above are selected. However, other thresholds may be chosen in alternative embodiments. The corresponding feature sets are shown in FIG. 13.

The selected features are subjected to PCA for dimensionality reduction. In the individualized embodiment, dimensionality reduction is carried out for each participant separately, whereas in the generalized embodiment, the combined dataset is used. After computing the corresponding principal components, the first n components are kept and classification accuracy on the validation data is computed. If the inclusion of the (n+1)th component does not improve the accuracy, n is taken to be the reduced dimension. The reduced dimensions for the generalized embodiment and statistics of reduced dimensions for 32 individualized embodiments are shown in FIG. 14.

Figure 15:
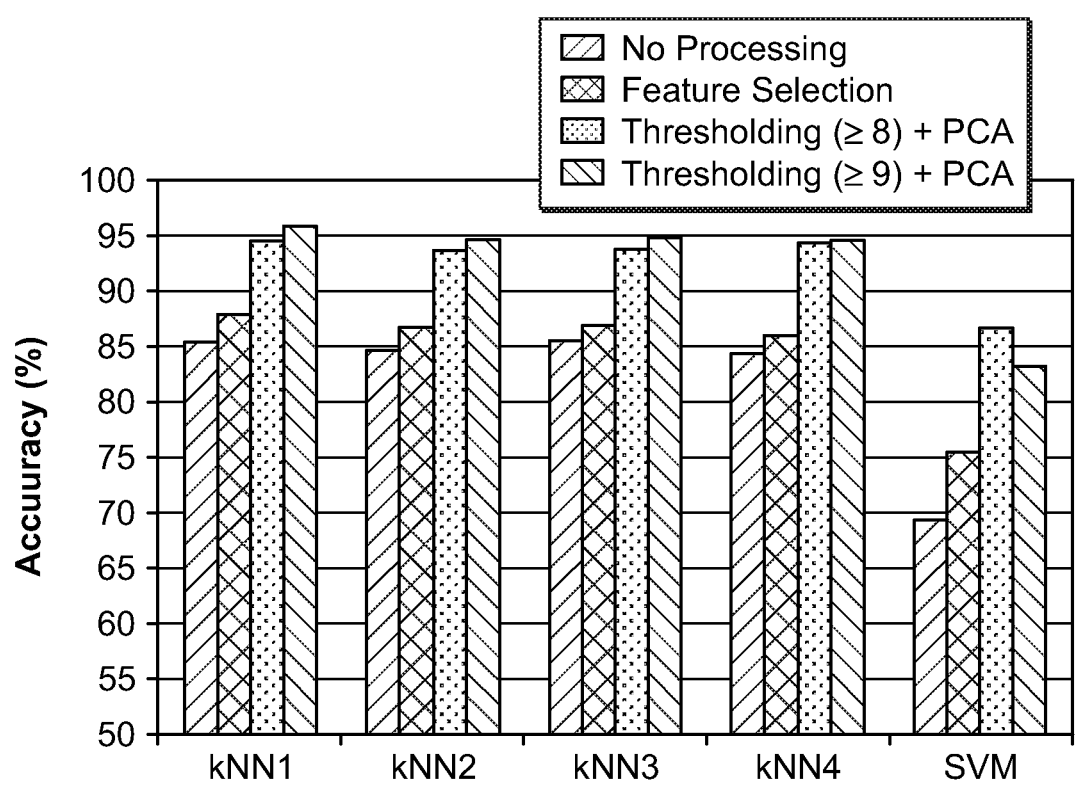
FIG. 15 is a chart showing the effect of feature selection, thresholding, and PCA on the accuracy of different classifiers according to an embodiment of the present invention.

The impact of forward feature selection with subset evaluation and PCA on the classification accuracy is demonstrated in FIG. 15 for kNN (k=1-4) and SVM. The first bar for each classifier represents the case when all 90 features were selected, hence, when no processing was done. Forward feature selection with subset evaluation followed by thresholding and PCA (third and fourth bars) can be seen to have the highest accuracies in all the cases. This is because forward feature selection with subset evaluation and PCA complement each other. Forward feature selection with subset evaluation is a supervised attribute selection method. It takes training data with labels as input and obtains the corresponding feature set.

However, due to the finite size of the training dataset, this method may eliminate some features that are indicators of stress. In order to overcome this problem, the advantage offered by unsupervised dimensionality reduction is exploited. After combining the reduced feature sets and selecting the ones above the threshold, PCA is applied. In PCA, the labels are not taken into account. Hence, the method is not adversely impacted by the training dataset size.

Using reduced dimensions, the performance of both the individualized and generalized embodiments are analyzed. The classification accuracy results are shown in boxplots in FIG. 16. FIG. 16(*c*) shows the definitions of the various boxplot parameters. For the individualized embodiment, the top and bottom of the boxplot indicates 75th and 25th percentiles, respectively. The whiskers show the maximum and minimum values without the outliers. The solid and dashed lines depict the median and mean of the individualized embodiments, respectively. The dotted line depicts the accuracy value for the generalized embodiment. FIGS. 16(*a*)

and 16(b) show the classification results for ECG threshold of ten and GSR+RESP+BO+BP threshold of eight and nine, respectively.

FIG. 16(a) shows the classification results obtained from kNN1 ($\mu$=94.5%), kNN2 ($\mu$=93.7%), kNN3 ($\mu$=93.8%), kNN4 ($\mu$=94.2%), and SVM ($\mu$=86.7%) for an ECG threshold of ten and GSR+RESP+BO+BP threshold of eight. FIG. 16(b) shows the classification results obtained from kNN1 ($\mu$=95.8%), kNN2 ($\mu$=94.7%), kNN3 ($\mu$=94.8%), kNN4 ($\mu$=94.5%), and SVM ($\mu$=83.2%) for an ECG threshold of ten and GSR+RESP+BO+BP threshold of nine. For the individualized embodiment, the mean of kNN classification accuracy varies between 93.7 and 94.5 percent in FIG. 16(a), and 94.5 and 95.8 percent in FIG. 16(b). The maximum accuracy (95.8 percent) is obtained when k=1. For SVM, the mean of the classification accuracy is 86.7 percent in FIG. 16(a) and 83.2 percent in FIG. 16(b). However, for the generalized embodiment, the corresponding maximum accuracies are 89.2 and 83.1 percent in FIG. 16(a), and 89.3 and 84.6 percent in FIG. 16(b) for kNN and SVM, respectively. Except for the result for SVM in FIG. 16(b), the individualized embodiment is observed to detect stress with higher accuracy relative to the generalized embodiment. Considering the negative effect of choosing a GSR+RESP+BO+BP threshold of nine in FIG. 15, this result is expected.

In addition to boxplots in FIG. 10, the 95 percent confidence interval (CI) was also computed for classification accuracies of the individualized embodiment. With an ECG threshold of ten and GSR+RESP+BO+BP threshold of eight, the corresponding 95 percent CIs are (92.5, 96.5 percent) for kNN1, (91.8, 95.6 percent) for kNN2, (91.8, 95.9 percent) for kNN3, (92.0, 96.5 percent) for kNN4, and (83.6, 89.7 percent) for SVM. With an ECG threshold of ten and GSR+RESP+BO+BP threshold of nine, the corresponding 95 percent CIs are (94.0, 97.5 percent) for kNN1, (92.8, 96.5 percent) for kNN2, (92.8, 96.7 percent) for kNN3, (92.4, 96.6 percent) for kNN4, and (79.9, 86.5 percent) for SVM. Both FIG. 16 and the CIs indicate that SoDA provides high stress detection accuracy. The accuracy difference between the two embodiments is due to the fact that stress impacts different individuals in slightly different ways. Thus, a model derived from a population of individuals cannot be expected to be as accurate as the model derived from just the individual.

SoDA enables stress detection in real-time. As shown in FIG. 17, the stress detection stage requires approximately 0.3 s for computing the feature values from WMS data. The measurements are based on a computing device such as a MacBook Pro with a processor such as a 2.5 GHz Intel Core i7 processor. Since WMS data are continuously collected, this enables the system to provide real-time stress tracking.

Stress Alleviation

If stress is detected, SoDA offers stress therapy and modifies the stress alleviation protocol based on the data collected. FIG. 18 shows the stress alleviation protocol. After the user makes use of the suggested stress mitigation technique, the relevant feature values are traced. If these newly obtained feature values have a tendency towards the 'no stress' case, SoDA continues to suggest the current stress mitigation technique for a period of time; otherwise, it suggests the next technique. This period of time can be modified by the user. According to the protocol in FIG. 18, when the stress alleviation technique is observed to reduce stress level for 60 s, the system transitions to the stress detection stage, and checks the user's stress level. If the user is classified as 'stressed' again, then the stress alleviation stage continues with the stress reduction technique.

To determine whether the proposed technique is working or not, a majority vote based on all the selected feature value trends is carried out. The feature set used in this stage is not the same with the features used for stress detection. This is because not all features behave the same way when a stressor is applied versus when stress mitigation is applied. For example, even when the body begins to relax, the impact on blood pressure is not immediate. Hence, features derived from blood pressure are not used in the stress alleviation step. In this case, feature values should have an immediate response and should be robust to biological differences. Thus, the features that are appropriate for indicating stress alleviation are selected separately using a feature selection process similar to the one used for stress detection. The aim of stress mitigation techniques is to help the user reach a relaxed state faster than when no such therapeutic technique is employed.

The features that were found to be the most reliable and robust to biological differences at this stage were: R-R interval, heart rate (HR), and ratio of low frequency to high frequency band power (LF/HF) of the ECG signal. Hence, they were chosen for the generalized embodiment. However, for the individualized embodiment, the system is designed to be more flexible. It allows the choice of additional features to respond to the needs of the user more effectively. After the application of stress therapy, if SoDA finds the traced values of the selected features indicate recovery from stress, the therapy is continued. Otherwise, the next stress reduction technique is suggested to the user.

FIGS. 19 and 20 show various statistics derived from the physiological signals for the generalized embodiment. For the three selected features, the statistics are derived over the 0-50 s and 60-120 s intervals. In the case of tasks T1-T4, no stress therapy is employed for the duration (120 s) of the stressful task. However, in the case of tasks T5-T8, starting from the 50th second, stress alleviation technique is used, however, without removing the stressor from the environment. Since stress mitigation needs some time to have an impact, the feature values are calculated 10 s after the start of the therapy.

First, in order to compare the effectiveness of the stress mitigation techniques, feature values are calculated for the 0-50 s duration for both without and with therapy cases. Since the therapy does not start until the 50th second, these values can be expected to be approximately equal for the same tasks. In other words, the same tasks should stress the participant to the same degree. Fly sound, IAPS, and ice test were verified to satisfy this condition. However, when the physiological signals were analyzed for task T1 (memory game), it was observed that the participants had an excessive stress response. This may have been because memory game was the first task the participants carried out. Even though the participants wore the sensors for some time to become comfortable with them and were given practice tests, their stress levels were different for the practice and real tests. Thus, their stress responses were different the first time they were asked to play the memory game (task T1) and the second time (task T6). Due to this reason, the effectiveness of the corresponding stress alleviation technique (classical music) could not be analyzed.

For the remaining therapies, when the stress mitigation techniques provide better results than the 'no therapy' case, the data are shown in non-italicized form, else in italicized, in FIGS. 19 and 20. Increase in the R-R interval and decrease in HR and LF/HF indicate a more relaxed state. Within the same time interval, if the stress mitigation techniques bring these feature values to a more relaxed state, then the corresponding techniques can be concluded to be more effective than the 'no therapy' case. In general, the remaining three stress mitigation techniques were verified to be effective.

Next, the order of effectiveness for the stress mitigation techniques was analyzed. Considering the mean of the feature values, FIGS. 19 and 20 show that both micro-meditation (T5) and good news (T8) are effective. In the case of warm stone therapy, the heart rate is not observed to indicate fast relief compared to 'no therapy' even though the other two feature values do. Hence, warm stone is rated (at least for the generalized embodiment) the lowest. Between micro-meditation and good news, since micro-meditation increases the R-R interval more, it is ranked higher.

A similar analysis is performed for the individualized embodiment. The results for one of the participants are shown in FIGS. 21 and 22. As in the generalized embodiment, the corresponding feature values are expected to be close to each other for 0-50 s (in columns T2-T5, T3-T7, and T4-T8). However, due to the smaller amount of data available for a sole individual in the individualized embodiment, the corresponding feature values are not as close as in the case of the generalized embodiment. Still, since the corresponding values are comparable, the analysis of stress reduction techniques is carried out. In the individualized embodiment, as the system collects more data, it models the stress characteristics of the user more precisely. The individualized embodiment also provides an opportunity to include more features that are suitable to the individual in question. This also means that the therapy order can now be tailored to the individual. For example, inhalation duration was an additional feature that was found to be useful for this individual. Increase in the inhalation duration indicates reduced stress. Based on the bolded values in FIGS. 21 and 22, the best order for this individual can be concluded to be: warm stone (T7), good news (T8), and micro-meditation (T5).

As shown in FIG. 23, since the order is different from the generalized embodiment, the advantage of personalized stress therapy is evident. In other words, if the user selects the individualized embodiment, the recovery becomes faster than if the generalized embodiment is selected. However, as can be seen from FIGS. 19-22, either of the options provides faster relief than the 'no therapy' alternative.

Advantages

SoDA includes both stress detection and alleviation stages. The overall system is shown to respond in real-time with 95.8% stress detection accuracy. For the stress alleviation stage, the system is compared with the 'no therapy' baseline. For both the 'no therapy' baseline and stress alleviation stages, the same stressors are applied for the same time interval. Since the stress alleviation stage is found to provide faster relief, its effectiveness is verified. SoDA enables both automatic stress detection and alleviation in a user-transparent manner, and provides quantitative evaluations using multiple WMSs, stressors, and therapies. It also offers high classification accuracy.

As such, disclosed herein is an automatic stress detection and alleviation system that is adaptive and requires minimum user involvement. The system was designed, implemented, and analyzed with multiple options and stress mitigation techniques. The system was shown to be capable of responding to and reducing the stress level of its user more effectively than when 'no therapy' option is used. SoDA can provide two options to its user: 'individualized' and 'generalized'. The 'individualized' embodiment is more accurate (95.8% as opposed to 89.3% for the 'generalized' embodiment). However, it requires physiological training data to be collected from the user for the derivation of the model. The 'generalized' embodiment can be used as is.

It is understood that the above-described embodiments are only illustrative of the application of the principles of the present invention. The present invention may be embodied in other specific forms without departing from its spirit or essential characteristics. All changes that come within the meaning and range of equivalency of the claims are to be embraced within their scope. Thus, while the present invention has been fully described above with particularity and detail in connection with what is presently deemed to be the most practical and preferred embodiment of the invention, it will be apparent to those of ordinary skill in the art that numerous modifications may be made without departing from the principles and concepts of the invention as set forth in the claims.

What is claimed is:

1. A machine learning based stress detection and alleviation (SoDA) system for a user comprising a SoDA device configured with one or more processors that receive wearable medical sensor (WMS) data from a plurality of WMSs, the processors being programmed to:
preprocess the WMS data from each WMS via range normalization;
extract pluralities of features from the WMS data for each WMS;
remove correlated features from the pluralities of features to obtain a reduced set of features via supervised attribute selection, thresholding, and principal component analysis, wherein:
supervised attribute selection comprises choosing features based on their individual contribution to accuracy and their redundancy with respect to other features;
thresholding comprises removing features that appear less than a predetermined threshold when all data from supervised attribute selection is combined; and
principal component analysis comprises transforming the data from supervised attribute selection into a number of orthogonal variables, the number of orthogonal variables being determined when a classification accuracy stops increasing;
classify the reduced set of features to determine whether the user is stressed by applying a computational operation corresponding to one of a generalized stress model and an individualized stress model, the generalized stress model being based on WMS data obtained from a plurality of users, the individualized stress model being based on WMS data obtained from the user; and
when classification indicates the user is stressed, monitor a set of features from the WMS data that is different from the reduced set of features for a predetermined amount of time in response to a stress mitigation technique.

2. The system of claim 1, wherein the WMS data comprises electrocardiogram (ECG) data, galvanic skin response (GSR) data, respiration rate data, blood pressure data, and blood oximeter data.

3. The system of claim 1, wherein classifying the reduced set of features comprises performing binary classification via support vector machine (SVM) or k-nearest neighbor (kNN).

4. The system of claim 1, wherein the stress mitigation technique comprises one of listening to classical music, practicing micro-meditation, holding a warm stone, and receiving good news.

5. The system of claim 1, wherein the processors are further programmed to preprocess the WMS data via at least one of:
- removing outlier data and replacing the outlier data with at least one of upper and lower thresholds; and
- denoising the WMS data with one or more filters.

6. The system of claim 1, wherein supervised attribute selection further comprises forward feature selection and subset evaluation.

7. The system of claim 1, wherein for the generalized stress model, the set of features from the WMS data that is different from the reduced set of features comprises R-R interval, heart rate, and ratio of low frequency to high frequency band power (LF/HF) of an electrocardiogram (ECG) signal.

8. The system of claim 1, wherein for the individualized stress model, the set of features from the WMS data that is different from the reduced set of features comprises R-R interval, heart rate, inhalation duration, and ratio of low frequency to high frequency band power (LF/HF) of an electrocardiogram (ECG) signal.

9. The system of claim 1, wherein the processors are further programmed to perform majority voting among the set of features from the WMS data that is different from the reduced set of features to indicate whether the stress mitigation technique reduced stress in the user after the predetermined amount of time.

10. The system of claim 9, wherein the processors are further programmed to monitor the set of features from the WMS data that is different from the reduced set of features for the predetermined amount of time in response to a second stress mitigation technique when the majority voting indicates the user continues to be stressed.

11. The system of claim 9, wherein the majority voting indicates the stress mitigation technique reduced stress when more than half of a count of the set of features from the WMS data that is different from the reduced set of features show a reduction in stress, wherein for the generalized stress model, showing a reduction in stress comprises at least one of an increase in R-R interval, a decrease in heart rate, and a decrease in a ratio of low frequency to high frequency band power (LF/HF) of an electrocardiogram (ECG) signal.

12. The system of claim 9, wherein the majority voting indicates the stress mitigation technique reduced stress when more than half of a count of the set of features from the WMS data that is different from the reduced set of features show a reduction in stress, wherein for the individualized stress model, showing a reduction in stress comprises at least one of an increase in R-R interval, a decrease in heart rate, an increase in inhalation duration, and a decrease in a ratio of low frequency to high frequency band power (LF/HF) of an electrocardiogram (ECG) signal.

13. A machine learning based method for stress detection and alleviation (SoDA) for a user of a SoDA device, the SoDA device including one or more processors, the method comprising:
- receiving wearable medical sensor (WMS) data from a plurality of WMSs;
- preprocessing the WMS data from each WMS via range normalization;
- extracting pluralities of features from the WMS data for each WMS;
- removing correlated features from the extracted pluralities of features to obtain a reduced set of features via supervised attribute selection, thresholding, and principal component analysis, wherein:
  - supervised attribute selection comprises choosing features based on their individual contribution to accuracy and their redundancy with respect to other features;
  - thresholding comprises removing features that appear less than a predetermined threshold when all data from supervised attribute selection is combined; and
  - principal component analysis comprises transforming the data from supervised attribute selection into a number of orthogonal variables, the number of orthogonal variables being determined when a classification accuracy stops increasing;
- classifying the reduced set of features in order to determine whether the user is stressed by applying a computational operation corresponding to one of a generalized stress model and an individualized stress model, the generalized stress model being based on WMS data obtained from a plurality of users, the individualized stress model being based on WMS data obtained from the user; and
- when classification indicates the user is stressed, monitoring a set of features from the WMS data that is different from the reduced set of features for a predetermined amount of time in response to a stress mitigation technique.

14. The method of claim 13, wherein the WMS data comprises electrocardiogram (ECG) data, galvanic skin response (GSR) data, respiration rate data, blood pressure data, and blood oximeter data.

15. The method of claim 13, wherein classifying the reduced set of features comprises performing binary classification via support vector machine (SVM) or k-nearest neighbor (kNN).

16. The method of claim 13, wherein the stress mitigation technique comprises one of listening to classical music, practicing micro-meditation, holding a warm stone, and receiving good news.

17. The method of claim 13, further comprising performing majority voting among the set of features from the WMS data that is different from the reduced set of features to indicate whether the stress mitigation technique reduced stress in the user after the predetermined amount of time.

18. The method of claim 17, further comprising monitoring the set of features from the WMS data that is different from the reduced set of features for the predetermined amount of time in response to a second stress mitigation technique when the majority voting indicates the user continues to be stressed.

19. A non-transitory computer-readable medium having stored thereon a computer program for execution by a processor configured to perform a machine learning based method for stress detection and alleviation of a user, the method comprising:
- receiving wearable medical sensor (WMS) data from a plurality of WMSs;
- preprocessing the WMS data from each WMS via range normalization;
- extracting pluralities of features from the WMS data for each WMS;
- removing correlated features from the extracted pluralities of features to obtain a reduced set of features via supervised attribute selection, thresholding, and principal component analysis, wherein:

supervised attribute selection comprises choosing features based on their individual contribution to accuracy and their redundancy with respect to other features;

thresholding comprises removing features that appear less than a predetermined threshold when all data from supervised attribute selection is combined; and principal component analysis comprises transforming the data from supervised attribute selection into a number of orthogonal variables, the number of orthogonal variables being determined when a classification accuracy stops increasing;

classifying the reduced set of features in order to determine whether the user is stressed by applying a computational operation corresponding to one of a generalized stress model and an individualized stress model, the generalized stress model being based on WMS data obtained from a plurality of users, the individualized stress model being based on WMS data obtained from the user; and when classification indicates the user is stressed, monitoring a set of features from the WMS data that is different from the reduced set of features for a predetermined amount of time in response to a stress mitigation technique.

20. The medium of claim 19, wherein the WMS data comprises electrocardiogram (ECG) data, galvanic skin response (GSR) data, respiration rate data, blood pressure data, and blood oximeter data.

21. The medium of claim 19, wherein classifying the reduced set of features comprises performing binary classification via support vector machine (SVM) or k-nearest neighbor (kNN).

22. The medium of claim 19, wherein the stress mitigation technique comprises one of listening to classical music, practicing micro-meditation, holding a warm stone, and receiving good news.

23. The medium of claim 19, wherein the method further comprises performing majority voting among the set of features from the WMS data that is different from the reduced set of features to indicate whether the stress mitigation technique reduced stress in the user after the predetermined amount of time.

24. The medium of claim 23, wherein the method further comprises monitoring the set of features from the WMS data that is different from the reduced set of features for the predetermined amount of time in response to a second stress mitigation technique when majority voting indicates the user continues to be stressed.

* * * * *